US010059722B2

(12) United States Patent
Aube et al.

(10) Patent No.: US 10,059,722 B2
(45) Date of Patent: Aug. 28, 2018

(54) CEPHALOSPORIN DERIVATIVES AND METHODS OF USE

(71) Applicants: University of Kansas, Lawrence, KS (US); Cornell University, Ithaca, NY (US)

(72) Inventors: Jeffrey Aube, Lawrence, KS (US); Carl Nathan, Larchmont, NY (US); Robert Smith, Lawrence, KS (US); Ben S. Gold, Millburn, NJ (US); Paul Hanson, Lawrence, KS (US); Chunjing Liu, Lawrence, KS (US); Lester Allen Mitscher, Lawrence, KS (US); Maneesh Pingle, Huntington, NY (US); Frank John Schoenen, Lawrence, KS (US)

(73) Assignee: UNIVERSITY OF KANSAS, Lawrence, KS (US)

(*) Notice: Subject to any disclaimer, the term of this patent is extended or adjusted under 35 U.S.C. 154(b) by 0 days.

(21) Appl. No.: 14/439,373

(22) PCT Filed: Nov. 4, 2013

(86) PCT No.: PCT/US2013/068245
§ 371 (c)(1),
(2) Date: Apr. 29, 2015

(87) PCT Pub. No.: WO2014/071283
PCT Pub. Date: May 8, 2014

(65) Prior Publication Data
US 2015/0322087 A1 Nov. 12, 2015

Related U.S. Application Data

(60) Provisional application No. 61/796,128, filed on Nov. 2, 2012.

(51) Int. Cl.
C07D 501/60 (2006.01)
C07D 501/16 (2006.01)
A61K 31/545 (2006.01)
C07D 499/44 (2006.01)
C07D 277/06 (2006.01)
C07D 417/12 (2006.01)
C07D 513/04 (2006.01)
A61K 45/06 (2006.01)
A61K 31/426 (2006.01)
A61K 31/427 (2006.01)
A61K 31/429 (2006.01)
A61K 31/43 (2006.01)
A61K 31/431 (2006.01)
A61K 31/4725 (2006.01)
A61K 31/546 (2006.01)

(52) U.S. Cl.
CPC .......... *C07D 501/16* (2013.01); *A61K 31/426* (2013.01); *A61K 31/427* (2013.01); *A61K 31/429* (2013.01); *A61K 31/43* (2013.01); *A61K 31/431* (2013.01); *A61K 31/4725* (2013.01); *A61K 31/545* (2013.01); *A61K 31/546* (2013.01); *A61K 45/06* (2013.01); *C07D 277/06* (2013.01); *C07D 417/12* (2013.01); *C07D 499/44* (2013.01); *C07D 513/04* (2013.01)

(58) Field of Classification Search
None
See application file for complete search history.

(56) References Cited

U.S. PATENT DOCUMENTS

| | | | | |
|---|---|---|---|---|
| 3,781,283 A | * | 12/1973 | Bormann et al. .... | C07D 205/08 540/218 |
| 3,926,984 A | * | 12/1975 | Teller ................... | C07D 499/00 540/222 |
| 4,211,702 A | * | 7/1980 | Hatfield ............... | C07D 499/00 540/215 |
| 6,440,462 B1 | | 8/2002 | Raneburger et al. ......... | 424/489 |
| 2011/0190253 A1 | | 8/2011 | Blanchard | |

FOREIGN PATENT DOCUMENTS

| | | | | |
|---|---|---|---|---|
| EP | 0268343 A2 | * | 5/1988 | .............. C12P 35/00 |
| JP | 53050195 A | * | 5/1978 | |
| WO | WO0200163 | | 1/2002 | |
| WO | WO-02096430 A1 | * | 12/2002 | ........... C07D 279/06 |

OTHER PUBLICATIONS

Banker, Gilbert. Modern Pharmaceutics 3rd ed. Marcel Dekker, Inc. New York, 1996.*
Shiozaki, Masao. Tetrahedron (1980), 36(19), 2735-40.*
Alpegiani, Marco. Synlett Letters (1997) 322-324.*
Davis, Michael. Aust. J. Chem. (1987) 1519-26.*
Archer, R.A. & Kitchell, B.S. "Chemistry of Cephalosporin Antibiotics. VI.[1] Carbamate Formation in Aqueous Bicarbonate Solutions of 7-ACA" J. Org. Chem. 1966 31:3409-11.
Batchelor et al. "Synthesis of Penicillin: 6-Aminopenicillanic Acid in Penicillin Fermentation" Nature 1959 183:257.
CID 23676814 [online]; Create Data: Feb. 5, 2008 from http://pubchem.ncbi.nlm.nih.gov/;2D-structure.
Cynamon, M.H. & Palmer, G.S. "In Vitro Activity of Amoxicillin in Combination with Clavulanic Acid Against *Mycobacterium tuberculosis*" Antimicrobial agents and chemotherapy 1983 24(3):429-431.
Finland, M. "Twenty-fifth Anniversary of the Discovery of Aureomycin: The Place of the Tetracyclines in Antimicrobial Therapy" Clin. Pharmacol. Ther. 1974 15:3-8.
Fleming, A. "On the Antibacterial Action of Cultures of a Penicillium, with Special Reference to their Use in the Isolation of *B. Influenzae*" Br. J. Exp. Pathol. 1929 10:226-230.

(Continued)

Primary Examiner — Deepak R Rao
Assistant Examiner — Laura M Daniel

(57) ABSTRACT

This invention provides cephalosporin derivatives for killing or inhibiting the spread of microorganisms such as non-replicating *Mycobacterium tuberculosis* and in the treatment of infectious disease.

6 Claims, 1 Drawing Sheet

(56) References Cited

OTHER PUBLICATIONS

Frank et al. "A Simple, Inexpensive Apparatus for Performance of Preparative Scale Solution Phase Multiple Parallel Synthesis of Drug Analogs. I. Preparation of a Retrospective Library of Quinolone Antiinfective Agents" Comb. Chem. High-Throughput Screen. 1998 1:56-70.
Holten, K.B. & Onusko, E.M. "Appropriate Prescribing of Oral Beta-Lactam Antibiotics" Am. Family Physician 2000 62:611-620.
Hugonnet et al."Meropenem-Clavulanate is Effective Against Extensively Drug-Resistant *Mycobacterium tuberculosis*" Science 2009 323:1215-8.
Kline et al. "Antimicrobial Effects of Novel Siderophores Linked to β-Lactam Antibiotics" Bioorgn. Med. Chem.2000 8:73-93.
Lagodsky, H. "Acquisition des Substances Antibiotiques" Biol. Med. (Paris) 1951 40:2-81.
McGuire et al. "Ilotycin, A New Antibiotic" Antimicrob. Chemother. 1952 2:281-283.
Metlay et al. "Tensions in Antibiotic Prescribing" J. Gen. Inter. Med. 2002 17:87-94.
Mitscher, L.A. "Coevolution: Mankind and Microbes" J. Nat. Prod. 2008 71:497-509.
Sheehan, J.C. & Henery-Logan, K.R. "A General Synthesis of the Penicillins" J. Am. Chem. Soc. 1959 81:5838.
Veinberg et al. "Recent Trends in the Design, Synthesis and Biological Exploration of β-Lactams" Curr. Med. Chem. 2014 21:393-416.
Waksman et al. "Isolation of Streptomycin-producing Strains of Streptomyces Griseus" J. Bacteriol. 1946 52:393-7.
International Search Report and Written Opinion in PCT/US13/68245, dated Mar. 7, 2014, PCT.
International Preliminary Examination Report on Patentability in PCT/US13/68245, dated May 5, 2015, PCT.

* cited by examiner

CEPHALOSPORIN DERIVATIVES AND METHODS OF USE

This application is a U.S. National Stage Application of PCT/US2013/068245 filed Nov. 4, 2013 and claims benefit of priority from U.S. Provisional Application Ser. No. 61/796,128, filed Nov. 2, 2012, the contents of each of which are incorporated herein by reference in their entirety.

BACKGROUND OF THE INVENTION

The β-lactam ring (Hoten & Onusko (2000) *Am. Family Physician* 62:611-620) is part of the structure of several antibiotic families, principally the penicillin derivatives, cephalosporins and related compounds, which are therefore also called β-lactam antibiotics (Gilchrist (1997) *Heterocyclic Chemistry* Harlow: Longman). As a group, these drugs are active against many gram-positive, gram-negative and anaerobic organisms. These antibiotics work by inhibiting the bacterial cell wall synthesis (Levy (1992) *The Antibiotics Paradox* Plenum Press: New York). This has a lethal effect on bacteria.

The discovery of antibiotics that can be used systemically is the most important medical event in the twentieth century. The story of the discovery by Sir Alexander Fleming of the penicillins in 1929 is well-known (Fleming (1929) *Br. J. Exp. Pathol.* 10:226-230). The introduction of penicillin into clinical trials in 1941 was followed in short order by the discovery of a plethora of penicillins and cephalosporins, streptomycin (Waksman, et al. (1946) *J. Bacteriol.* 52:393-7), chloramphenicol (Lagodsky, (1951) *Biol. Med.* (Paris) 40:2-81), tetracycline (Finland (1974) *Clin. Pharmacol. Ther.* 15:3-8), and erythromycin (McGuire, et al. (1952) *Antimicrob. Chemother.* 2:281-283). However, shortly after the clinical introduction of antibiotics, reports of microbial resistance during the course of treatment began to appear in the literature. Penicillin was first used in 1941, and by 1942 publications relating to resistance appeared (Remmelkamp & Kamp (1942) *Proc. Soc. Exptl. Biol. Med.* 51:356-360). Resistance was noted with increasing frequency until this phenomenon could no longer be ignored (Mitscher (2008) *J. Nat. Prod.* 71:497-509). Societal impact of antibiotic resistance is a major public health problem (Metlay, et al. (2002) *J. Gen. Inter. Med.* 17:87-94). To avoid the development of antibiotic resistance, newer antibiotics should be reserved for patients infected with resistant bacteria.

Effective strategies to deal with the resistance problem are relatively few. On approach includes the use of a combination therapy such as meropenem and clavulanate, which has been shown to kill replicating and non-replicating *Mycobacterium tuberculosis* (Hugonnet, et al. (2009) *Science* 323:1215-8). Other strategies include searching for novel antibiotics, modification of existing antibiotics, synthesis and directed biosynthesis of novel antimicrobials, inhibition of bacterial enzymes that inactivate antibiotics, use of combinations of antibiotics, immunostimulants, and the identification of new targets for antibiotics. This effort subsequently led to combinatorial methods for synthesis of analogs of β-lactams (Frank, et al. (1998) *Comb. Chem. High-Throughput Screen.* 1:56-70; Kline, et al. (2000) *Bioorgn. Med. Chem.* 8:73-93), which have a number of targets, many of which are not related to peptidoglycan biosynthesis and many of which are found in eukaryotic cells (Veinberg, et al. (2013) *Curr. Med. Chem.* Vol. 20).

The availability of 6-aminopenicillanic acid (6-APA, 1; Batchelor, et al. (1959) *Nature* 183:257; Sheehan & Henery-Logan (1959) *J. Am. Chem. Soc.* 81:5838) has made possible the synthesis of new, improved penicillins when covalently linked to a side-chain moiety.

The cephalosporin nucleus, 7-aminodesacetoxy cephalosporanic acid (7-ADCA, 2; Archer & Kitchell (1966) *J. Org. Chem.* 31:3409-11), was derived from cephalosporin C and is an analog of the penicillin nucleus 6-APA. Modification of the 7-ADCA side-chains could also result in the development of useful antibiotic agents.

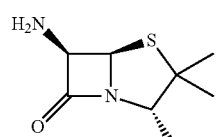

1

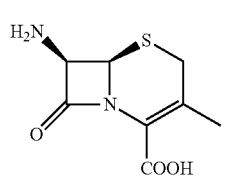

2

SUMMARY OF THE INVENTION

This invention is a compound having the structure of Formula I, II, III, IV or V, or a pharmaceutically acceptable salt or prodrug thereof:

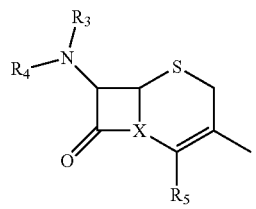

Formula I

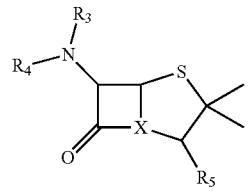

Formula II

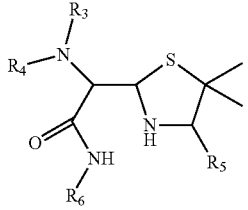

Formula III

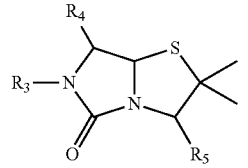

Formula IV

-continued

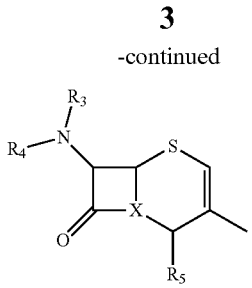

Formula V wherein
$R_3$ is H, $CH_3$ or $-CR_7$;
$R_4$ and $R_5$ are independently $C_1$-$C_{10}$ alkyl, $-COO^-$, $-COOH$, $-CR_7$, $-C(=O)OR_7$, $-C(=O)COR_7$, $-C(=O)OCR_7$, $-C(=O)C(-CH_3)OR_7$, $-CH_2OR_7$, $-C(=O)CH_2CH_2R_7$ or $-NHR_6$;
$R_6$ is $C_1$-$C_{10}$ alkyl, $C_3$-$C_7$ cycloalkyl, aryl, heteroaryl, or $-CR_7$;
$R_7$ is $C_1$-$C_{10}$ alkyl, $C_2$-$C_{10}$ alkenyl, $C_2$-$C_{10}$ alkynyl, $C_3$-$C_7$ cycloalkyl, aryl, or heteroaryl; and
X is N or O.

Pharmaceutical compositions and methods of using the compounds and compositions to kill or inhibit the spread of microorganisms and prevent, mitigate or treat an infectious disease are also provided.

DETAILED DESCRIPTION OF THE INVENTION

Figure 1:
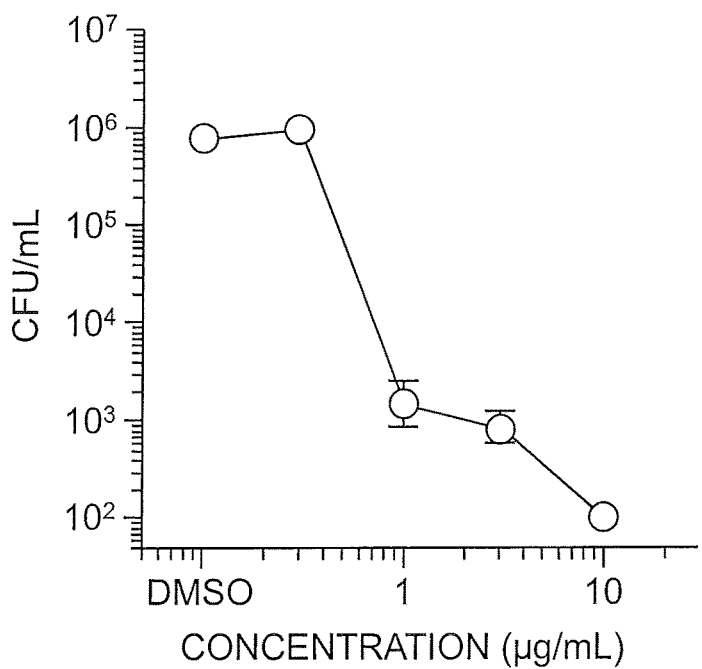
FIG. 1 shows that cephalosporin 13 has cidal activity against non-replicating wild-type *Mycobacterium tuberculosis* (Mtb). Mtb was at an $OD_{580}$ of 0.01 and exposed to compound 13 for 7 days at 1% $O_2$ and enumerated on 7H11-OADC agar plates that support replication. Activity was clavulanate-independent. At 10 μg/mL, compound 13 killed Mtb below the limit of detection (100 colony forming units).

The long duration of chemotherapy to treat tuberculosis is thought to be due to non-replicating *Mycobacterium tuberculosis* bacteria that are phenotypically resistant (non-heritable resistance) to chemotherapy by factors of host immunity. Failure to eradicate non-replicating *M. tuberculosis* by standard chemotherapy leaves the human host susceptible to recrudescence of latent bacilli and development of tuberculosis.

Cephalosporins are broad spectrum antibiotics used in human medicine to kill replicating bacteria by blocking peptidoglycan biosynthesis. However, cephalosporins are not generally associated with having activity against *M. tuberculosis*. Furthermore, since peptidoglycan biosynthesis would likely not play an essential role when cells are not actively growing, the identification of 6-APA and 7-ADCA derivatives, as described herein, with activity against non-replicating *M. tuberculosis* was unexpected. Derivatization of 6-APA resulted in a range of compounds that contained amide and ester motifs within the low molecular weight structures. These were associated with the N-alkylation of β-lactam ring, the esterification of carboxylic acid moiety on the thiazolane ring, the amide formation on nucleophilic opening of the β-lactam ring using primary amines, and also the $CO_2$-assisted rearrangement of the β-lactam ring. The resulting compounds have a more restricted antimicrobial spectra, more favorable absorption patterns and/or reduced undesirable effects and are stable under acid conditions and in the presence of reactive nitrogen intermediates or oxidation. Furthermore, these compounds were rapidly hydrolyzed in mouse serum, an effect which was not prevented by addition of 'bulky' groups such as aromatic groups near the ester. In addition, the compounds have limited toxicity against HepG2 cells thereby indicating their use in the treatment of tuberculosis.

Therefore, this invention provides cephalosporin derivatives containing azetidine and oxetane rings, amide and ester motifs, and pharmaceutically acceptable salts and prodrugs thereof, and their use in the treatment and/or prevention of disease caused by microorganisms. In one embodiment the cephalosporin derivatives of the invention are derivatives of 6-APA or 7-ADCA. In particular, the invention encompass compounds having the structure of Formula I, II, III, IV or V:

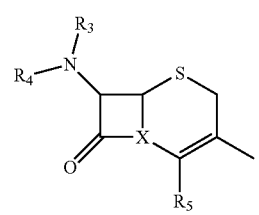

Formula I

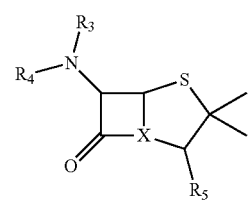

Formula II

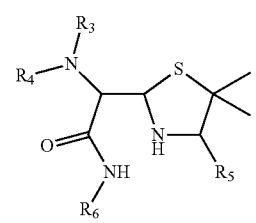

Formula III

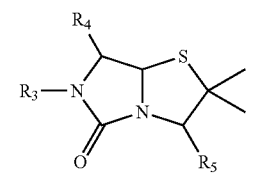

Formula IV

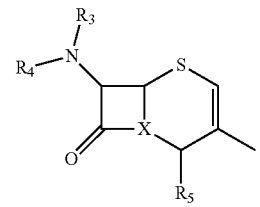

Formula V wherein
R$_3$ is H, CH$_3$ or —CR$_7$;
R$_4$ and R$_5$ are independently C$_1$-C$_{10}$ alkyl, —COO$^-$, —COOH, —CR$_7$, —C(=O)OR$_7$, —C(=O)COR$_7$, —C(=O)OCR$_7$, —C(=O)C(—CH$_3$)OR$_7$, —CH$_2$OR$_7$, —C(=O)CH$_2$CH$_2$R$_7$ or —NHR$_6$;
R$_6$ is C$_1$-C$_{10}$ alkyl, C$_3$-C$_7$ cycloalkyl, aryl, heteroaryl, or —CR$_7$;
R$_7$ is C$_1$-C$_{10}$ alkyl, C$_2$-C$_{10}$ alkenyl, C$_2$-C$_{10}$ alkynyl, C$_3$-C$_7$ cycloalkyl, aryl, or heteroaryl; and
X is N or O.

For the groups herein, the following parenthetical subscripts further define the groups as follows: "(C$_n$)" defines the exact number (n) of carbon atoms in the group. For example, "C$_1$-C$_{10}$-alkyl" designates those alkyl groups having from 1 to 15 carbon atoms (e.g., 1, 2, 3, 4, 5, 6, 7, 8, 9, or 10, or any range derivable therein (e.g., 3-10 carbon atoms)).

The term "alkyl" refers to a non-aromatic monovalent group with a saturated carbon atom as the point of attachment, a linear or branched, cyclo, cyclic or acyclic structure, and no carbon-carbon double or triple bonds. The groups, —CH$_3$, —CH$_2$CH$_3$, —CH$_2$CH$_2$CH$_3$, —CH(CH$_3$)$_2$, —CH(CH$_2$)$_2$, —CH$_2$CH$_2$CH$_2$CH$_3$, —CH(CH$_3$)CH$_2$CH$_3$, —CH$_2$CH(CH$_3$)$_2$, —C(CH$_3$)$_3$, and —CH$_2$C(CH$_3$)$_3$ are non-limiting examples of alkyl groups.

The term "alkenyl" refers to a monovalent group with a nonaromatic carbon atom as the point of attachment, a linear or branched, cyclo, cyclic or acyclic structure, at least one nonaromatic carbon-carbon double bond, and no carbon-carbon triple bonds. Non-limiting examples of alkenyl groups include —CH=CH$_2$, —CH=CHCH$_3$, —CH=CHCH$_2$CH$_3$, —CH$_2$CH=CH$_2$, —CH$_2$CH=CHCH$_3$, and —CH=CH—C$_6$H$_5$.

The term "alkynyl" refers to a monovalent group with a nonaromatic carbon atom as the point of attachment, a linear or branched, cyclo, cyclic or acyclic structure, and at least one carbon-carbon triple bond. The groups —C≡CH, —C≡CCH$_3$, —C≡CC$_6$H$_5$ and —CH$_2$C≡CCH$_3$, are non-limiting examples of alkynyl groups.

"Cycloalkyl" means a non-aromatic mono- or multicyclic ring system including about 3 to 7 carbon atoms, preferably about 3 to about 6 carbon atoms. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

The term "aryl" refers to a monovalent group with an aromatic carbon atom as the point of attachment, said carbon atom forming part of a six-membered aromatic ring structure wherein the ring atoms are all carbon, and wherein the monovalent group is composed of carbon and hydrogen. Non-limiting examples of aryl groups include phenyl, methylphenyl, (dimethyl)phenyl, ethylphenyl, propylphenyl, —C$_6$H$_4$CH(CH$_3$)$_2$, —C$_6$H$_4$CH(CH$_2$)$_2$, methylethylphenyl, vinylphenyl, naphthyl, and the monovalent group derived from biphenyl.

The term "heteroaryl" refers to a monovalent group with an aromatic carbon atom as the point of attachment, said carbon atom forming part of an aromatic ring structure wherein at least one of the ring atoms is nitrogen, oxygen or sulfur, and wherein the monovalent group is composed of carbon, hydrogen, aromatic nitrogen, aromatic oxygen or aromatic sulfur. Non-limiting examples of aryl groups include acridinyl, furanyl, imidazoimidazolyl, imidazopyrazolyl, imidazopyridinyl, imidazopyrimidinyl, indolyl, indazolinyl, methylpyridyl, oxazolyl, phenylimidazolyl, pyridyl, pyrrolyl, pyrimidyl, pyrazinyl, quinolyl, quinazolyl, quinoxalinyl, tetrahydroquinolinyl, thienyl, triazinyl, pyrrolopyridinyl, pyrrolopyrimidinyl, pyrrolopyrazinyl, pyrrolotriazinyl, pyrroloimidazolyl, chromenyl (where the point of attachment is one of the aromatic atoms), and chromanyl (where the point of attachment is one of the aromatic atoms).

Any of the groups described herein may be unsubstituted or optionally substituted. Substitutions typically replace an available hydrogen with an alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, alkoxyalkoxy, acyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, or heterocyclyl.

Any undefined valency on an atom of a structure shown in this application implicitly represents a hydrogen atom bonded to the atom.

Exemplary substituted and unsubstituted alkyl, alkenyl, alkynyl, cycloalkyl, aryl, and heteroaryl groups of compounds within the scope of Formula I-V are provided in the Schemes, Tables and Examples herein.

In one embodiment, the invention embraces one or more novel compounds as disclosed in Scheme 1, Scheme 2, Scheme 3, Scheme 4, Scheme 6, Scheme 7, Scheme 8 or Scheme 9. In another embodiment, the invention embraces one or more novel compounds as disclosed in Table 1, Table 5 or Table 6. In a further embodiment, the invention embraces one or more of Compounds 4a-4b, 5a-5k, 6a-6f, 7, 8a-8d, 9a-9b, 10a-10b, 11a-11c, 12a-12d or 13-97. In yet other embodiments, the invention excludes Compounds 4a (CAS 20676-17-9), 5a (CAS 2315-05-1), 5d (CAS 1256-06-0), 5i (CAS 21650-32-8), 5k (CAS 1256-06-0), 11c (CAS 1135316-73-2), 12b (CAS 1135416-15-7), 12c (CAS 1135197-43-1), 13 (CAS 1135197-53-3), 14 (CAS 36746-17-5), 40 (CAS 114018-78-9) and 80 (CAS 10209-06-0).

"Pharmaceutically acceptable salts" means salts of compounds of the invention which are pharmaceutically acceptable, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and di-carboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

Compounds of the invention may also exist in prodrug form. Since prodrugs are known to enhance numerous desirable qualities of pharmaceuticals, e.g., solubility, bioavailability, manufacturing, etc., the compounds employed in some methods of the invention may, if desired, be delivered in prodrug form. Thus, the invention contemplates prodrugs of compounds of the present invention as well as methods of delivering prodrugs. Prodrugs of the compounds of this invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a patient, cleaves to form a hydroxy, amino, or carboxylic acid, respectively. For example, a compound having a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methane-sulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

Therapeutics, including compositions containing the cephalosporin derivatives of the invention, can be prepared in physiologically acceptable formulations, such as in pharmaceutically acceptable carriers, using known techniques. For example, a cephalosporin derivative is combined with a pharmaceutically acceptable excipient to form a pharmaceutical composition.

The compositions of the invention may be administered in the form of a solid, liquid or aerosol. Examples of solid compositions include pills, creams, soaps and implantable dosage units. Pills may be administered orally. Therapeutic creams and anti-bacterial soaps may be administered topically. Implantable dosage units may be administered locally, for example, in the lungs, or may be implanted for sustained release of the therapeutic composition, for example, subcutaneously. Examples of liquid compositions include formulations adapted for injection intramuscularly, subcutaneously, intravenously, intraarterially, and formulations for topical and intraocular administration. Examples of aerosol formulations include inhaler formulations for administration to the lungs.

A sustained release matrix, as used herein, is a matrix made of materials, usually polymers, which are degradable by enzymatic or acid/base hydrolysis, or by dissolution. Once inserted into the body, the matrix is acted upon by enzymes and body fluids. The sustained release matrix is chosen desirably from biocompatible materials, including, but not limited to, liposomes, polylactides, polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipds, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide.

The dosage of the composition will depend on the condition being treated, the particular compound used, and other clinical factors, such as weight and condition of the patient, and the route of administration. A suitable dosage may range from 100 to 0.1 mg/kg. A more preferred dosage may range from 50 to 0.2 mg/kg. A more preferred dosage may range from 25 to 0.5 mg/kg. Tablets or other forms of media may contain from 1 to 1000 mg of one or more cephalosporin derivatives. Dosage ranges and schedules of administration similar to ethambutol or other anti-tuberculosis drugs may be used.

The compounds of this invention can be used alone or in combination with conventional antimicrobial agents used in the treatment of infectious disease. In particular, the invention includes a combination therapy composed of one or more cephalosporin derivatives as presently described together with one or more antitubercular agents, including but not limited to, isoniazid, rifampicin, pyrazinamide, ethionamide, ethambutol, streptomycin, fluoroquinolones (e.g., moxifloxacin), linezolid, β-lactams (e.g., meropenem), β-lactams in conjunction with β-lactamase inhibitors (e.g., clavulanate), and experimental drugs such as PA-824 and R207910 (i.e., Bedaquiline sold under the tradename SIRTURO).

Furthermore, one or more cephalosporin derivatives may be administered in combination with other compositions and procedures for the treatment of other disorders occurring in combination with mycobacterial disease. For example, tuberculosis frequently occurs as a secondary complication associated with acquired immunodeficiency syndrome (AIDS). Therefore, patients undergoing AIDS treatment may benefit from the therapeutic methods and compositions described herein.

Cephalosporin derivatives of the invention are of particular use in killing or inhibiting the spread of microorganisms, in particular bacterial agents. Particular examples of such infectious agents include, but are not limited to, *Actinomyces* spp., *Bacillus* spp., *Bacterioides* spp., *Bartonella* spp., *Bordetella* spp., *Borrelia* spp., *Brucella* spp., *Burkholderia* spp., *Campylobacter* spp., *Chlamydia* spp., *Clostridium* spp., *Corynebacterium* spp., *Ehrlichia* spp., *Enterococcus* spp., *Escherichia* spp., *Francisella* spp., *Haemophilus* spp., *Helicobacter* spp., *Klebsiella* spp., *Legionella* spp., *Leptospira* spp., *Listeria* spp., *Mycobacterium* spp., *Mycoplasma* spp., *Neisseria* spp., *Nocardia* spp., *Propionibacterium* spp., *Pseudomonas* spp., *Rickettsia* spp., *Salmonella* spp., *Shigella* spp., *Staphylococcus* spp., *Streptococcus* spp., *Treponema* spp., *Vibrio* spp., and *Yersinia* spp.

In particular, the methods and compositions of this invention are effective in killing or inhibiting the spread of the microorganism, *M. tuberculosis*. In this respect, the methods and compositions of this invention are intended for the treatment of mycobacterial infections in human, as well as other animals. For example, this invention may be particularly useful for the treatment of cows infected by *M. bovis*. Moreover, the compositions and methods of the invention are particular useful in the treatment of infections in which some of the mycobacteria are non-replicating.

This invention further provides methods and compositions useful for the prevention, mitigation and/or treatment of infectious disease caused by one or more of the microorganisms described above. In this respect, the invention includes methods for the prevention, mitigation and/or treatment of infectious diseases including by not limited to, tuberculosis, leprosy, Crohn's Disease, lyme disease, catscratch disease and Rocky Mountain Spotted Fever. As used herein, the term "tuberculosis" is intended to include disease states usually associated with infections caused by mycobacteria species of the *M. tuberculosis* complex. The term "tuberculosis" is also associated with mycobacterial infections caused by mycobacteria other than *M. tuberculosis*. Other mycobacterial species include *M. avium-intracellulare, M. kansarii, M. fortuitum, M. chelonae, M. leprae, M. africanum*, and *M. microti, M. avium paratuberculosis, M. intracellulare, M. scrofulaceum, M. xenopi, M. marinum*, and *M. ulcerans*.

As used herein, the term "treatment" or "treating" means any therapeutic intervention in a mammal, preferably a human or any other animal suffering from a bacterial infection, such that symptoms and bacterial numbers are reduced or eliminated. "Prevention" or "preventing" refers to prophylactic treatment causing the clinical symptoms not to develop, e.g., preventing infection from occurring and/or developing to a harmful state. "Mitigation" or "mitigating" means arresting the development of clinical symptoms, e.g., stopping an ongoing infection to the degree that it is no longer harmful, or providing relief or regression of clinical symptoms, e.g., a decrease in fluid loss resulting from an infection.

In accordance with this invention, a subject in need of prevention, mitigation or treatment is administered an effective amount of a composition containing one or more cephalosporin derivatives disclosed herein, thereby preventing, mitigating, or treating a bacterial infection. Subjects benefiting from the method of the invention include those having (e.g., exhibiting signs or symptoms) or at risk of having (e.g., a subject exposed to a contaminated food or water source) a bacterial infection as described herein.

The terms "effective amount" means a dosage sufficient to provide prevention, mitigation and/or treatment of a bacterial infection. The amount and dosage regimen of the composition of the invention to be administered is determined in the light of various relevant factors including the purpose of administration (e.g., prevention, mitigation or treatment), the age, sex and body weight of an individual subject, and/or the severity of the subject's symptoms. In this respect, the compositions of the invention can be administered under the supervision of a medical specialist, or may be self-administered.

In addition to treatment, it is contemplated that the compounds of this invention can labeled and used as to identify target molecules that bind or interact with the compounds of the invention. In this regard, the present also includes a compound having the structure of Formula I, II, III, IV or V, wherein said compound is labeled, e.g., with biotin, a radiolabel, fluorescein, or other fluorescent dye. By way of illustration, a pre-clicked cephalosporin-biotin molecule, pre-clicked cephalosporin-fluorescein molecule and $^{13}C$-labeled compound are shown below.

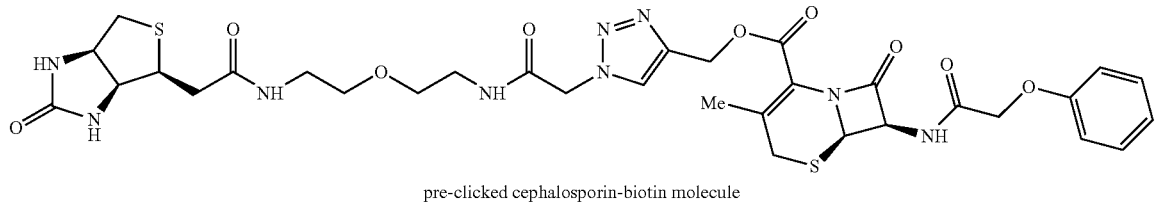

pre-clicked cephalosporin-biotin molecule

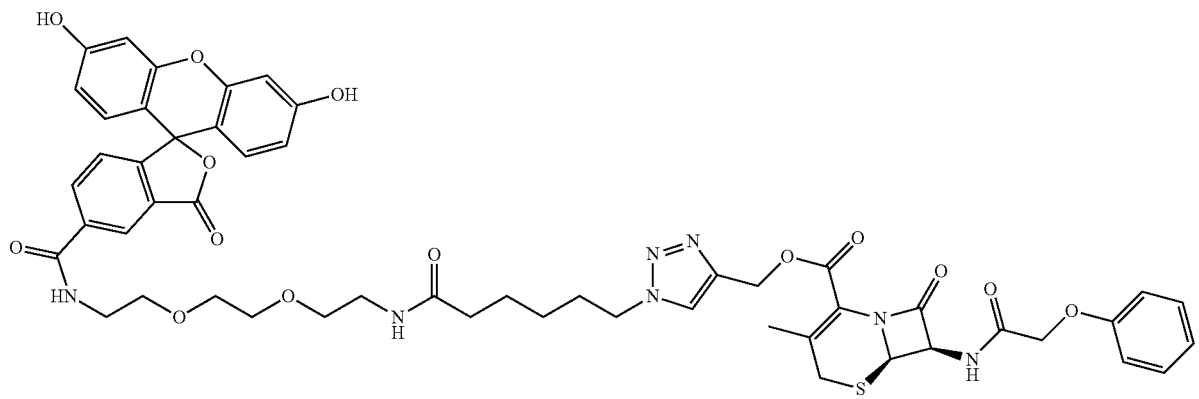

pre-clicked cephalosporin-fluorescein molecule

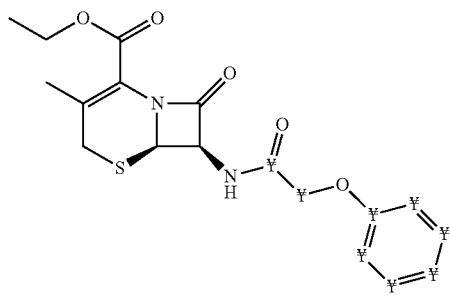

$^{13}$C (¥) labeled

The invention will be further described in the following examples, which do not limit the scope of the invention described in the claims.

EXAMPLE 1

Materials and Methods

Column chromatography was carried out by employing silica gel (230-400 mesh). Thin-layer chromatography (TLC) was performed on a silica gel w/uv254 UNIPLATE. Melting points were determined using a Barnstead International MET-TEMP capillary Melting Point Apparatus. IR spectra were measured with a PERKIN ELMER Spectrum One FTIR spectrometer. $^1$H NMR and $^{13}$C NMR spectra were recorded on a 400 MHz spectrometer (400 and 100 MHz, respectively), or a 500 MHz spectrometer (500 and 125.5 MHz, respectively). NMR spectra were recorded in CDCl$_3$ unless otherwise indicated. Abbreviations are as follows: s, singlet; d, doublet; t, triplet; q, quartet; br s, broad singlet; br d, broad doublet. High-resolution mass spectrometry (HRMS) spectra were obtained on a double-focusing mass spectrometer.

Penicillin V: Potassium (2S,5R,6R)-3,3-dimethyl-7-oxo-6-(2-phenoxyacetamido)-4-thia-1-azabicyclo[3.2.0]heptane-2-carboxylate (4a)

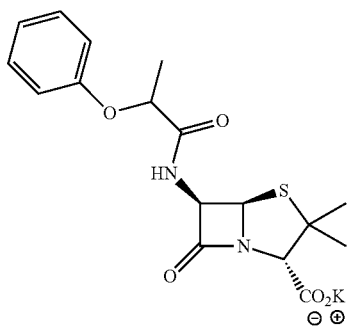

4a

To a cooled and stirred solution of 2.76 g (12.5 mmol) of 6-APA in 60 mL of water containing 5.25 g (62.5 mmol) of sodium bicarbonate, a solution of 2.76 g (16.2 mmol) of phenoxyacetyl chloride in 5 mL of acetone was added in 1 minute. The resulting mixture was stirred vigorously for 20 minutes, while the temperature was kept at 10-15° C. The clear solution was extracted twice with 15 mL portions of methyl isobutyl ketone (MIBK). The organic extracts were discarded. The clear aqueous solution was cooled to 5-10° C. and acidified to pH 2 with a cold 5 M sulfuric acid solution. The acidified aqueous solution was extracted with 50 mL MIBK twice. The MIBK extract was separated, washed with cold water, and dried for 10 minutes over anhydrous sodium sulfate. After filtration, 10 mL of a 25% solution of potassium 2-ethylhexanoate in butanol was added. The white crystalline material was collected by filtration, washed on the filter with dry acetone and dried in vacuum, yield 3.5 g (80%) white solid 4a. mp: 210-211° C. (dec.); $^1$H NMR (DMSO-d$_6$, 400 MHz): δ 8.42 (d, J=8.0 Hz, 1H), 7.27 (m, 2H), 6.92 (m, 3H), 5.41 (m, 2H), 4.62 (d, J=2.2 Hz, 2H), 3.88 (s, 1H), 1.52 (s, 3H), 1.46 (s, 3H); $^{13}$C NMR (DMSO-d$_6$, 100 MHz): δ 172.8, 169.0, 168.0, 158.0, 129.9, 121.6, 115.0, 74.5, 67.3, 66.6, 65.0, 57.7, 32.6, 27.8.

Potassium (2S,5R,6R)-3,3-dimethyl-7-oxo-6-(2-phenoxypropanamido)-4-thia-1-azabicyclo[3.2.0]heptane-2-carboxylate (4b)

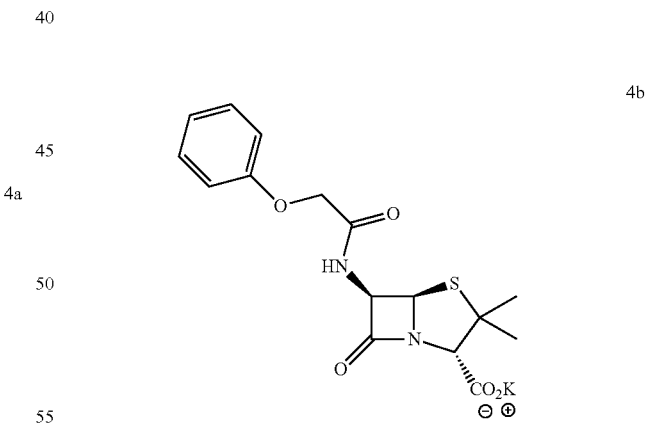

4b

The procedure for the synthesis of 4a was also used for the preparation of 4b. Yield: 70%; mp: 230-232° C. (dec.); $^1$H NMR (DMSO-d$_6$, 400 MHz): δ 8.58 (d, J=7.88 Hz, 1H), 7.29-7.22 (m, 2H), 6.94-6.87 (m, 3H), 5.35-5.27 (m, 1H), 5.26-5.24 (m, 1H), 4.93-4.86 (m, 1H), 3.81 (d, J=4.4 Hz, 1H), 1.51 (s, 3H), 1.42 (s, 3H), 1.33 (s, 3H); $^{13}$C NMR (DMSO-d$_6$, 100 MHz): δ 172.55, 171.60, 168.73, 157.52, 129.96, 121.54, 115.33, 74.81, 72.83, 67.38, 65.08, 57.85, 32.41, 27.89, 19.25; HRMS (FAB) m/z calcd for C$_{17}$H$_{20}$KN$_2$O$_5$S [M+H]$^+$ 403.0730; found 403.0743.

(2S,5R,6R)-Methyl 3,3-dimethyl-7-oxo-6-(2-phenoxyacetamido)-4-thia-1-azabicyclo[3.2.0]heptane-2-carboxylate (5a)

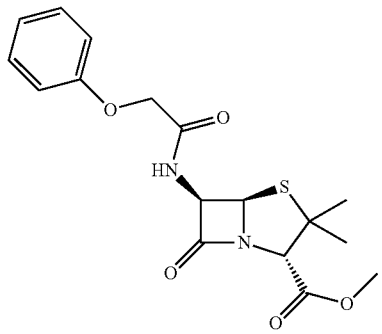

5a

Penicillin V 4a (388 mg, 1.0 mmol) was suspended in 10 mL of dimethylformamide, 1.4 g (12 mmol) of methyl iodide was added and stirred for 1 hour at room temperature. After most of the solvent was removed under reduced pressure, the mixture was directly loaded on silica gel column for chromatography with EtOAc/hexane (1:9) as eluent to yield colorless oil product 5a. Yield: 65%; $^1$H NMR (400 MHz): δ 6.91-7.32 (m, 5H), 5.70-5.74 (m, 1H), 4.45 (d, J=4.28 Hz, 2H), 4.46 (5, 1H), 3.71 (s, 2, 3H), 1.61 (s, 3H), 1.50 (s, 3H); $^{13}$C NMR (100 MHz): δ 173.0, 168.0, 167.8, 156.9, 129.8, 114.7, 70.4, 67.7, 67.1, 58.0, 52.4, 31.7, 26.8; HRMS (FAB) m/z calcd for $C_{17}H_{21}N_2O_5S$ [M+H]$^+$ 365.1170; found 365.1192.

(2S,5R,6R)-nonyl 3,3-dimethyl-7-oxo-6-(2-phenoxyacetamido)-4-thia-1-azabicyclo[3.2.0]heptane-2-carboxylate (5b)

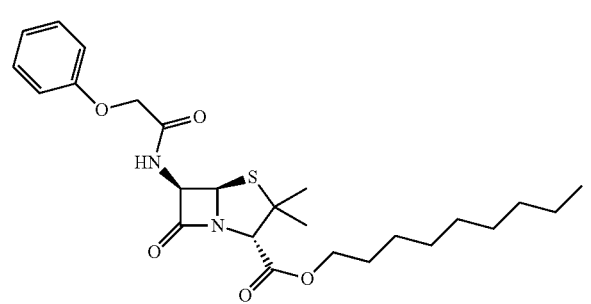

5b

The procedure for the synthesis of phenoxypropanyl-penicillin methyl ester 5a was also used for the preparation of 5b. Yield: 63%; $^1$H NMR (400 MHz): 56.91-7.32 (m, 5H), 5.76 (d, J=4.24 Hz, 1H), 5.59 (d, J=4.24 Hz, 1H), 4.57 (d, J=4.0 Hz, 3H), 4.47 (s, 1H), 4.17 (m, 2H), 1.62-1.64 (m, 4H), 1.6 (s, 3H), 1.5 (s, 3H), 1.29-1.49 (m, 12H), 0.9-1.1 (m, 3H); $^{13}$C NMR (100 MHz): δ 172.9, 167.8, 167.6, 156.9, 129.8, 114.7, 70.5, 67.8, 67.1, 65.9, 64.6, 58.1, 32.0, 31.8, 29.4, 29.1, 28.4, 26.8, 25.8, 22.6, 14.1; HRMS (FAB) m/z calcd for $C_{25}H_{37}N_2O_5S$ [M+H]$^+$477.2423; found 477.2430.

(2S,5R,6R)-cyclohexylmethyl 3,3-dimethyl-7-oxo-6-(2-phenoxyacetamido)-4-thia-1-azabicyclo[3.2.0]heptane-2-carboxylate (5c)

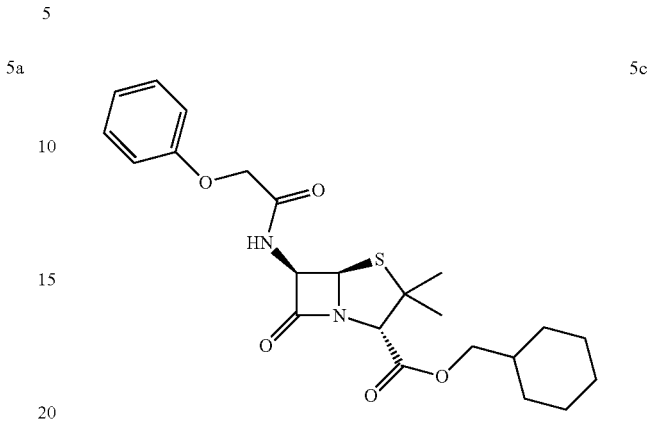

5c

The procedure for the synthesis of phenoxypropanyl-penicillin methyl ester 5a was also used for the preparation of 5c. Yield: 55%; $^1$H NMR (400 MHz): δ 7.37-7.31 (m, 3H), 7.06 (m, 1H), 6.92 (m, 1H), 5.75 (m, 1H), 5.59 (m, 1H), 4.47-4.57 (m, 3H), 3.44-4.02 (m, 2H), 1.77-1.63 (m, 6H), 1.60 (s, 3H), 1.55 (s, 3H), 1.13-1.01 (m, 5H); $^{13}$C NMR (100 MHz): δ 172.9, 167.8, 167.6, 156.9, 129.8, 122.3, 114.7, 70.9, 70.5, 67.8, 67.1, 64.7, 58.1, 36.8, 32.1, 29.6, 26.8, 26.2, 25.5; HRMS (FAB) m/z calcd for $C_{23}H_{31}N_2O_5S$ [M+H]$^+$ 447.1953; found 447.1964.

(2S,5R,6R)-benzyl 3,3-dimethyl-7-oxo-6-(2-phenoxyacetamido)-4-thia-1-azabicyclo[3.2.0]heptane-2-carboxylate (5d)

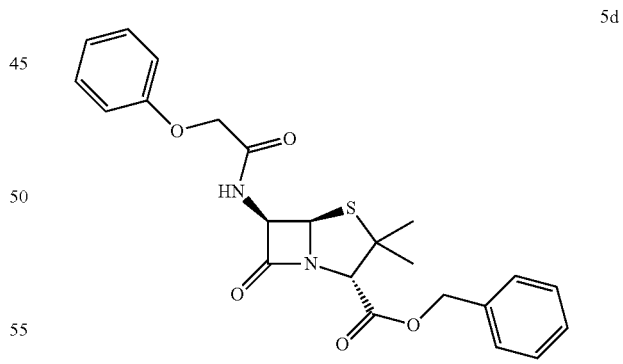

5d

The procedure for the synthesis of phenoxypropanyl-penicillin methyl ester 5a was also used for the preparation of 5d. Yield: 69%; $^1$H NMR (400 MHz): δ 6.94-7.37 (m, 10H), 5.57-5.76 (m, 1H), 5.61 (d, J=4.24 Hz, 1H), 5.22 (s, 2H), 4.53 (m, 3H), 1.59 (s, 3H), 1.44 (s, 3H); $^{13}$C NMR (100 MHz): δ 173.0, 167.8, 167.4, 156.9, 134.7, 129.8, 128.8, 128.7, 122.4, 114.8, 70.4, 67.8, 67.5, 67.1, 64.9, 58.1, 32.0, 26.7; HRMS (FAB) m/z calcd for $C_{23}H_{25}N_2O_5S$ [M+H]$^+$ 441.1484; found 441.1493.

(2S,5R,6R)-(1-(phenylsufonyl)-1H-indol-2-yl)methyl 3,3-dimethyl-7-oxo-6-(2-phenoxyacetamido)-4-thia-1-azabicyclo[3.2.0]heptane-2-carboxylate (5e)

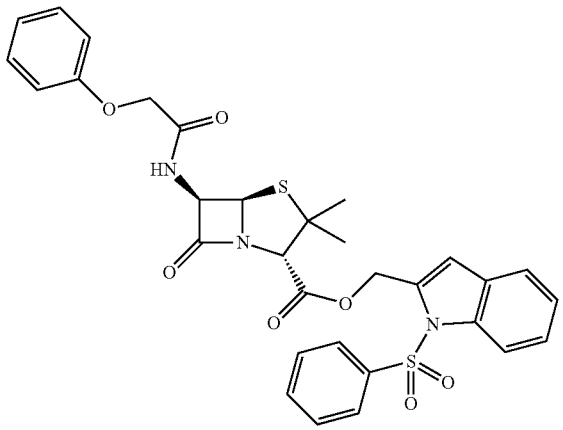

5e

The procedure for the synthesis of phenoxypropanyl-penicillin methyl ester 5a was also used for the preparation of 5e. Yield: 58%; $^1$H NMR (400 MHz): δ 8.11 (d, J=0.8 Hz, 1H), 7.79 (m, 1H), 7.46 (m, 2H), 7.32-7.48 (m, 7H), 7.06 (m, 1H), 6.93 (m, 2H), 6.81 (s, 1H), 5.75 (dd, J=4.0, 9.2 Hz, 1H), 5.61 (m, 2H), 4.57 (d, 4.28 Hz, 2H), 4.44 (s, 1H), 1.58 (s, 3H), 1.51 (s, 3H); $^{13}$C NMR (100 MHz): δ 173.1, 167.8, 167.1, 156.9, 138.6, 137.2, 134.1, 133.5, 129.8, 129.4, 128.6, 126.3, 125.7, 124.0, 122.4, 121.5, 114.7, 114.6, 114.2, 70.4, 67.7, 67.1, 64.9, 60.2, 58.0, 31.7, 26.7; HRMS (FAB) m/z calcd for $C_{31}H_{30}N_3O_7S_2$ [M+H]$^+$620.1525; found 620.1537.

(2S,5R,6R)-(5-methylisoxazol-3-yl)methyl 3,3-dimethyl-7-oxo-6-(2-phenoxyacetamido)-4-thia-1-azabicyclo[3.2.0]heptane-2-carboxylate (5f)

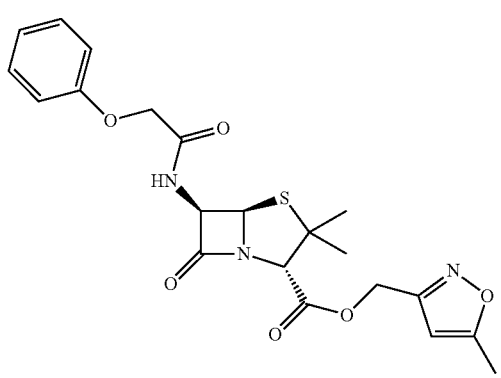

5f

The procedure for the synthesis of phenoxypropanyl-penicillin methyl ester 5a was also used for the preparation of 5f. Yield: 62%; $^1$H NMR (400 MHz): δ 7.36-7.32 (m, 2H), 7.01 (m, 1H), 6.90 (m, 2H), 6.04 (s, 1H), 5.72 (m, 1H), 5.71 (m, 1H), 5.57 (m, 2H), 4.52 (m, 3H), 2.42 (s, 3H), 1.58 (s, 3H), 1.47 (s, 3H); $^{13}$C NMR (100 MHz): δ 173.0, 170.6, 167.8, 167.1, 158.6, 156.9, 129.8, 122.3, 114.7, 101.3, 70.3, 67.7, 67.1, 64.8, 31.7, 26.8, 12.3; HRMS (FAB) m/z calcd for $C_{21}H_{24}N_3O_6S$ [M+H]$^+$446.1386; found 446.1390.

(2S,5R,6R)-benzo thiazol-2-ylmethyl 3,3-dimethyl-7-oxo-6-(2-phenoxyacetamido)-4-thia-1-azabicyclo[3.2.0]heptane-2-carboxylate (5g)

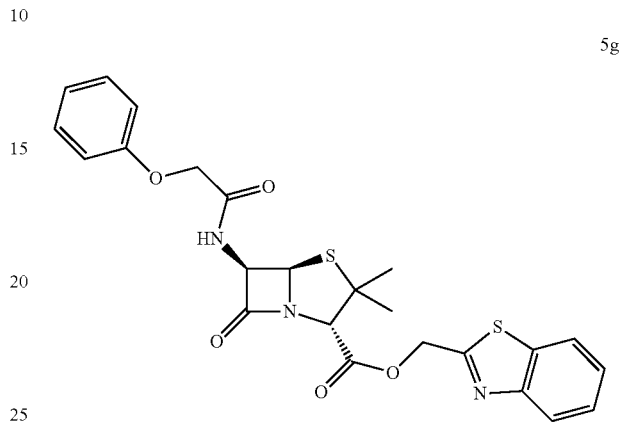

5g

The procedure for the synthesis of phenoxypropanyl-penicillin methyl ester 5a was also used for the preparation of 5g. Yield: 65%; $^1$H NMR (400 MHz): δ 8.05 (d, J=8.0 Hz, 1H), 7.93 (d, J=7.9 Hz, 1H), 7.28-7.54 (m, 5H), 7.05-6.93 (m, 3H), 5.79 (dd, J=4.28, 9.4 Hz, 1H), 5.64 (m, 1H), 5.59 (m, 2H), 4.61 (s, 1H), 4.57 (m, 2H), 1.65 (s, 3H), 1.55 (s, 3H); $^{13}$C NMR (100 MHz): δ 173.0, 167.8, 166.9, 163.8, 156.9, 152.7, 129.8, 126.5, 125.8, 123.5, 122.4, 121.8, 114.7, 70.4, 67.8, 67.1, 64.0, 58.1, 31.8, 27.0; HRMS (FAB) m/z calcd for $C_{24}H_{24}N_3O_5S_2$ [M+H]$^+$498.1157; found 498.1152.

(2S,5R,6R)-quinolin-8-ylmethyl 3,3-dimethyl-7-oxo-6-(2-phenoxyacetamido)-4-thia-1-azabicyclo[3.2.0]heptane-2-carboxylate (5h)

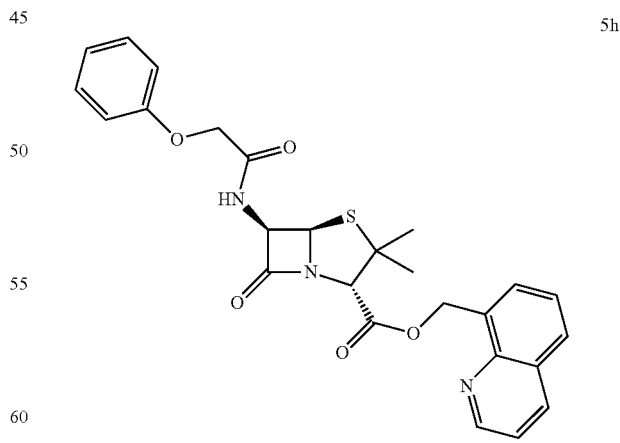

5h

The procedure for the synthesis of phenoxypropanyl-penicillin methyl ester 5a was also used for the preparation of 5h. $^1$H NMR (400 MHz): δ 8.95 (dd, J=1.72, 4.2 Hz, 1H), 8.18 (dd, J=1.72, 8.3 Hz, 1H), 7.84 (m, 1H), 7.80 (m, 1H), 7.47 (m, 1H), 7.45 (m, 1H), 7.31-7.29 (m, 3H), 7.02 (m, 1H), 6.92 (m, 2H), 5.89 (m, 2H), 5.70 (m, 1H), 5.60 (m, 1H), 4.54 (5, 1H), 1.53 (5, 3H), 1.46 (s, 3H); $^{13}$C NMR (100 MHz): δ 173.0, 167.8, 167.6, 156.9, 150.6, 146.1, 136.2, 129.8, 129.7, 128.9, 126.1, 122.3, 121.5, 114.7, 70.5, 67.7, 67.1, 65.0, 64.1, 58.0, 31.8, 26.7; HRMS (FAB) m/z calcd for $C_{26}H_{26}N_3O_5S$ [M+H]$^+$492.1593; found 492.1597.

(2S,5R,6R)-methyl 3,3-dimethyl-7-oxo-6-(2-phenoxypropanamido)-4-thia-1-azabicyclo[3.2.0]heptane-2-carboxylate (5i)

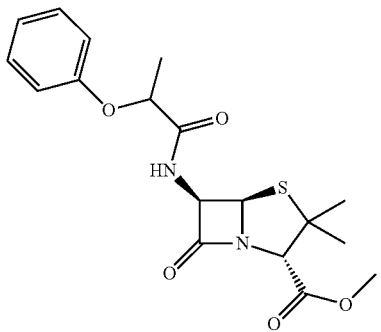

The procedure for the synthesis of phenoxypropanyl-penicillin methyl ester 5a was also used for the preparation of 5i. Yield: 42%; $^1$H NMR (400 MHz): δ 7.33-7.27 (m, 2H), 7.23 (d, J=7.6 Hz, 1H), 7.05-6.99 (m, 1H), 6.93-6.92 (m, 2H), 5.68-5.60 (m, 2H), 4.76 (dd, J=6.8, 13.5 Hz, 1H), 4.43 (s, 1H), 3.77 (s, 3H), 1.59 (d, J=6.8 Hz, 3H), 1.48 (s, 3H), 1.46 (s, 3H); $^{13}$C NMR (100 MHz): δ 173.35, 172.57, 171.83, 171.79, 168.10, 168.04, 156.68, 156.60, 129.83, 122.32, 115.64, 115.58, 74.98, 74.77, 70.51, 70.24, 67.81, 67.68, 64.59, 52.42, 52.40, 31.94, 31.37, 26.88, 26.46, 18.69, 18.50; HRMS (FAB) m/z calcd for $C_{18}H_{23}N_2O_5S$ [M+H]$^+$379.1327; found 379.1334.

(2S,5R,6R)-propyl 3,3-dimethyl-7-oxo-6-(2-phenoxypropanamido)-4-thia-1-azabicyclo[3.2.0]heptane-2-carboxylate (5j)

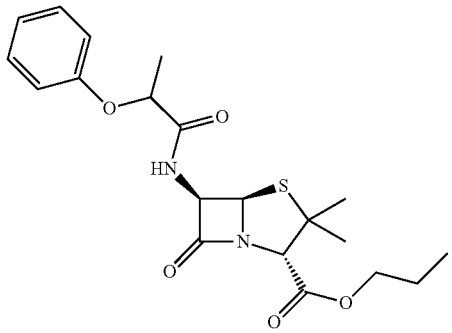

The procedure for the synthesis of phenoxypropanyl-penicillin methyl ester 5a was also used for the preparation of 5j. Yield: 43%; $^1$H NMR (400 MHz): δ 7.30-7.25 (m, 2H), 7.02-6.96 (m, 1H), 6.92-6.89 (m, 2H), 5.66-5.47 (m, 1H), 5.59 (s, 1H), 5.75-4.72 (m, 1H), 4.40 (s, 1H), 4.13-4.09 (m, 2H), 1.70-1.64 (m, 2H), 1.58 (d, J=7.4 Hz, 3H), 1.47 (s, 3H), 1.43 (s, s, 3H), 0.97-0.93 (m, 3H); $^{13}$C NMR (100 MHz): δ 173.26, 172.51, 171.77, 167.65, 156.70, 129.81, 122.29, 116.00, 115.42, 74.96, 74.78, 70.55, 70.30, 67.91, 67.78, 67.29, 64.54, 58.59, 58.13, 26.67, 26.28, 21.81, 18.69, 18.50, 10.45; HRMS (FAB) m/z calcd for $C_{20}H_{27}N_2O_5S$ [M+H]$^+$407.1640; found 407.1647.

(2S,5R,6R)-benzyl 3,3-dimethyl-7-oxo-6-(2-phenoxypropanamido)-4-thia-1-azabicyclo[3.2.0]heptane-2-carboxylate (5k)

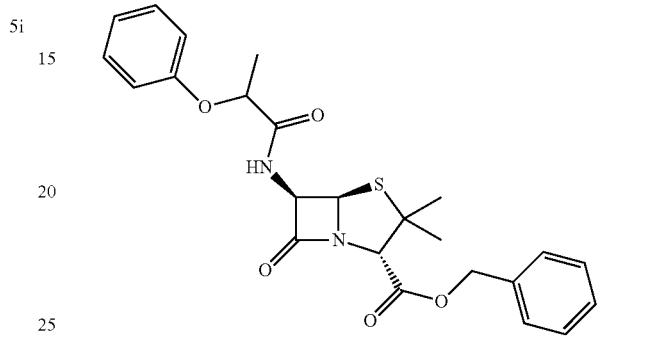

The procedure for the synthesis of phenoxypropanyl-penicillin methyl ester 5a was also used for the preparation of 5k. Yield: 42%; $^1$H NMR (400 MHz): δ 7.40-7.35 (m, 5H), 7.32-7.23 (m, 2H), 7.03-6.98 (m, 1H), 6.95-6.90 (m, 2H), 5.67-5.48 (m, 1H), 5.59 (s, 1H), 5.18 (s, 2H), 4.78-4.72 (m, 1H), 1.61-1.57 (m, 3H), 1.52 (s, 3H), 1.41 (s, 3H); $^{13}$C NMR (100 MHz): δ 173.31, 172.56, 171.78, 171.75, 167.47, 167.41, 156.71, 156.63, 134.70, 129.85, 129.84, 128.79, 128.75, 128.71, 122.35, 115.67, 115.60, 74.81, 74.76, 70.47, 70.23, 67.94, 67.81, 67.53, 64.72, 58.63, 58.17; HRMS (FAB) m/z calcd for $C_{24}H_{27}N_2O_5S$ [M+H]$^+$455.1640; found 455.1647.

(2R,4S)-methyl 2-((R)-2-(4-methoxybenzylamino)-2-oxo-1-(2-phenoxyacetamido)ethyl)-5,5-dimethyl-thiazolidine-4-carboxylate (6a)

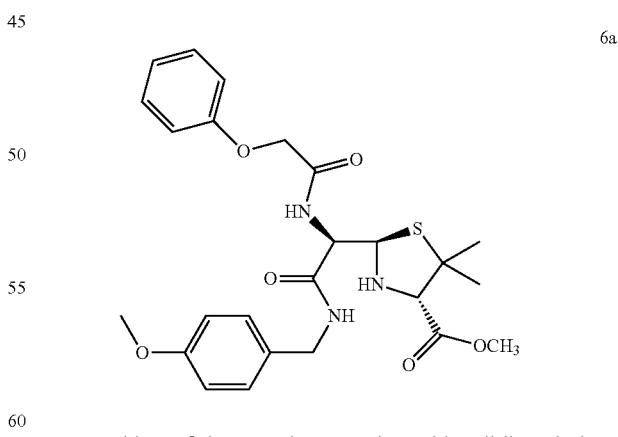

To achieve β-lactam ring opening, thiazolidine derivatives were synthesized from methyl ester of penicillin V (Styring & Chong (2006) Tetra. Lett. 47:1737-40; Holmes, et al. (1993) J. Med. Chem. 36:3129-36). The penicillin V methyl ester 5i 182.0 mg (0.5 mmol) was taken in a round-bottomed flask and 15 mL of dry methylene chloride was added. To this, benzyl amine 108.0 mg (1.0 mmol) was added at room temperature and stirred overnight. Water was added and extracted with methylene chloride (2×20 ml), washed with brine, organic layer was dried over sodium sulphate, concentrated and separated via column chromatography using 1:1 EtOAc/hexane on silica gel to yield product 6a as a semi-solid. Yield: 55%; $^1$H NMR (400 MHz): δ 7.61 (d, J=7.4 Hz, 1H), 7.21 (m, 4H), 7.20 (m, 2H), 7.03 (m, 1H), 6.99 (m, 1H), 6.86 (m, 2H), 6.85 (m, 3H), 5.23 (br s, 1H), 4.64 (m, 1H), 4.57 (m, 3H), 4.23 (m, 1H), 3.77 (s, 3H), 3.73 (s, 3H), 3.54 (br s, 1H), 1.48 (s, 3H), 1.18 (s, 3H); $^{13}$C NMR (100 MHz): δ 169.8, 168.9, 168.3, 159.0, 157.1, 129.7, 129.2, 122.0, 114.8, 114.1, 72.5, 67.2, 65.6, 58.0, 56.8, 55.2, 52.2, 43.1, 26.6, 26.5; HRMS (FAB) m/z calcd for $C_{25}H_{32}N_3O_6S$ [M+H]$^+$ 502.2011; found 502.1992.

(2R,4S)-methyl 2-((R)-2-(4-methoxyphenylamino)-2-oxo-1-(2-phenoxyacetamido)ethyl)-5,5-dimethyl-thiazolidine-4-carboxylate (6b)

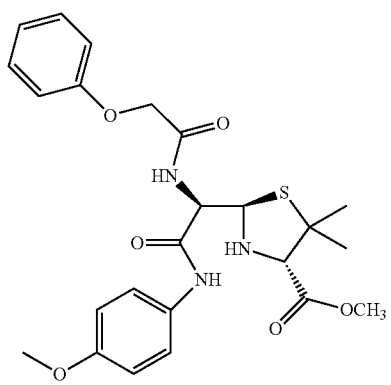

6b

The procedure for the synthesis of thiazolidine derivatives 6a was also used for the preparation of 6b. Yield: 62%; $^1$H NMR (400 MHz): δ 8.59 (s, 1H), 7.67 (d, J=6.4 Hz, 1H), 7.42-7.40 (m, 2H), 7.32 (m, 2H), 6.96 (m, 1H), 6.95 (m, 2H), 6.85 (m, 2H), 5.36 (m, 1H), 4.74 (m, 1H), 4.57 (m, 2H), 3.80 (s, 3H), 3.75 (s, 3H), 3.64 (br s, 1H), 1.55 (s, 3H), 1.24 (s, 3H); $^{13}$C NMR (100 MHz): δ 169.8, 169.3, 166.5, 157.1, 156.6, 129.7, 121.7, 114.8, 114.1, 72.7, 67.2, 65.3, 58.0, 57.2, 55.4, 52.3, 26.8, 26.4; HRMS (FAB) m/z calcd for $C_{24}H_{30}N_3O_6S$ [M+H]$^+$488.1855; found 488.1849.

(2R,4S)-methyl 5,5-dimethyl-2-((R)-2-oxo-1-(2-phenoxyacetamido)-2-(thiophen-3-ylmethylamino)ethyl) thiazolidine-4-carboxylate (6c)

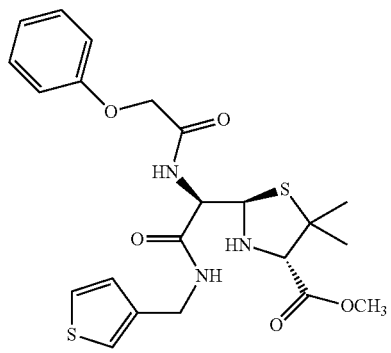

6c

The procedure for the synthesis of thiazolidine derivatives 6a was also used for the preparation of 6c. Yield: 63%; $^1$H NMR (400 MHz): δ 7.61 (d, J=7.56 Hz, 1H), 7.32-7.18 (m, 5H), 7.01-6.91 (m, 6H), 5.24 (br d, J=4.9 Hz, H), 4.72-6.62 (m, 2H), 4.52-4.42 (m, 3H), 3.73 (s, 3H), 3.56 (br s, 2H), 1.47 (s, 3H), 1.18 (s, 3H); $^{13}$C NMR (100 MHz): δ 169.8, 168.9, 168.4, 157.1, 140.2, 129.7, 126.9, 126.2, 125.2, 122.1, 114.8, 72.5, 672, 65.5, 58.0, 56.7, 52.2, 38.2, 26.6, 26.5; HRMS (FAB) m/z calcd for $C_{22}H_{28}N_3O_5S_2$ [M+H]$^+$ 478.1470; found 478.1475.

(2R,4S)-methyl 2-((R)-2-(benzylamino)-2-oxo-1-(2-phenoxyacetamido)ethyl)-5,5-dimethylthiazolidine-4-carboxylate (6d)

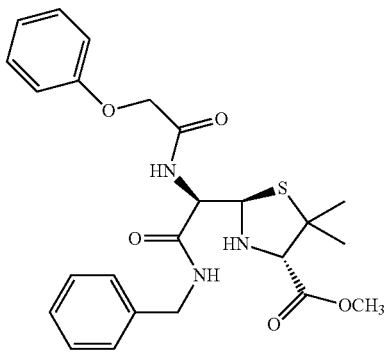

6d

The procedure for the synthesis of thiazolidine derivatives 6a was also used for the preparation of 6d. Yield: 54%; $^1$H NMR (400 MHz): δ 7.59 (d, 7036 Hz, 1H), 7.33-7.29 (m, 7H), 7.01 (m, 2H), 6.93 (m, 2H), 5.27 (br s, 1H), 4.61-4.56 (m, 4H), 4.51 (d, 6.8 Hz, 1H), 4.34 (dd, J=5.9, 14.7 Hz, 1H), 3.75 (s, 3H), 3.55 (br s, 2H), 1.48 (5, 3H), 1.20 (5, 3H); $^{13}$C NMR (100 MHz): δ 169.8, 168.9, 168.4, 157.1, 137.7, 129.7, 128.7, 127.9, 127.6, 122.1, 114.8, 107.9, 106.7, 103.2, 72.5, 67.2, 65.4, 57.9, 56.8, 52.2, 43.7, 26.5, 26.4; HRMS (FAB) m/z calcd for $C_{24}H_{30}N_3O_6S$ [M+H]$^+$ 472.1906; found 472.1910.

(2R,4S)-methyl 2-((R)-2-(cyclopropylamino)-2-oxo-1-(2-phenoxyacetamido)ethyl)-5,5-dimethyUhiazolidine-4-carboxylate (6e)

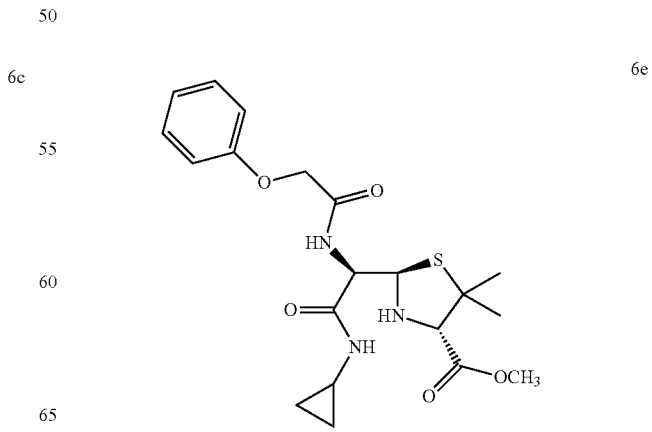

6e

The procedure for the synthesis of thiazolidine derivatives 6a was also used for the preparation of 6e. Yield: 64%; $^1$H NMR (400 MHz): δ 7.55 (d, J=7.7 Hz, 1H), 7.29 (m, 2H), 7.01-6.80 (m, 4H), 5.17 (d, J=6.1 Hz, 1H), 4.50 (m, 3H), 3.68 (s, 3H), 3.66 (s, 1H), 2.70 (m, 1H), 1.53 (s, 3H), 1.24 (m, 1H), 1.19 (s, 3H), 0.73 (m, 2H), 0.49 (m, 2H); $^{13}$C NMR (100 MHz): δ 170.1, 169.8, 168.9, 157.1, 129.7, 122.1, 114.7, 72.6, 67.2, 65.8, 58.2, 56.7, 52.2, 27.0, 26.6, 22.6, 6.50, 6.40; HRMS (FAB) m/z calcd for $C_{20}H_{28}N_3O_5S$ [M+H]$^+$422.1749; found 422.1739.

(2R,4S)-methyl 5,5-dimethyl-2-((R)-2-(non-ylamino)-2-oxo-1-(2-phenoxyacetamido)ethyl)thi-azolidine-4-carboxylate (6f)

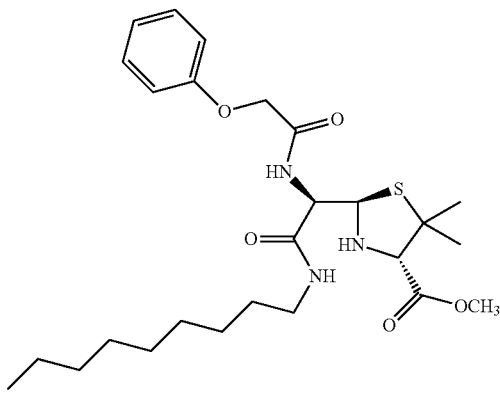

6f

The procedure for the synthesis of thiazolidine derivatives 6a was also used for the preparation of 6f. Yield: 58%; $^1$H NMR (400 MHz): δ 7.56 (m, 1H), 7.24 (m, 2H), 7.23-6.84 (m, 4H), 5.15 (m, 1H), 4.55 (m, 1H), 4.51 (m, 1H), 3.55 (m, 4H), 3.22 (m, 1H), 3.17-3.13 (m, 2H), 1.51 (s, 3H), 1.45 (m, 2H), 1.21-1.16 (m, 16H), 0.83 (m, 3H); $^{13}$C NMR (100 MHz): δ 169.8, 168.8, 168.6, 157.2, 129.6, 122.0, 114.7, 72.6, 67.2, 66.0, 58.2, 57.0, 52.1, 39.7, 31.8, 29.5, 29.4, 29.3, 29.2, 27.1, 26.9, 26.6, 22.6, 14.0; HRMS (FAB) m/z calcd for $C_{26}H_{42}N_3O_5S$ [M+H]$^+$508.2845; found 508.2828.

Disodium Salt of 8-Hydroxypenillic acid (3,3-dim-ethyl-8-oxo-4-thia-1,7-diazabicyclo[3.3.0]octane-2,6-dicarboxylic acid) (7)

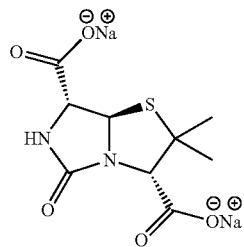

7

Compound 3 was prepared by a, modified method described in the art (Johnson & Hardcastle (1961) *J. Am. Chem. Soc.* 83:3534-35). 6-APA (1, 4.5 g) was dissolved in 100 mL of water containing 3.5 g (2 equiv.) of sodium bicarbonate. Carbon dioxide was bubbled through the stirred mixture at room temperature for 24 hours. The concentrated aqueous solution was then lyophilized overnight to yield 6.2 g (90%) of the product 7 as pale yellow powder. m.p. 228-230° C. (dec.); $^1$H NMR (D$_2$O, 400 MHz): δ 5.44 (d, J=2.0 Hz, 1H), 4.15 (s, 1H), 4.13 (d, J=2.0 Hz, 1H), 1.47 (s, 3H), 1.42 (s, 3H); $^{13}$C NMR (D$_2$O, 125 MHz): δ 177.45, 175.93, 164.41, 73.56, 69.39, 59.47, 57.68, 31.46, 25.82. HRMS (FAB) m/z calcd for $C_9H_{11}N_2Na_2O_5S$ [M+H]$^+$ 305.0185; found 305.0174.

(3S,7R,7aR)-dimethyl 2,2-dimethyl-5-oxohexahy-droimidazo[5,1-b]thiazole-3,7-dicarboxylate (8a)

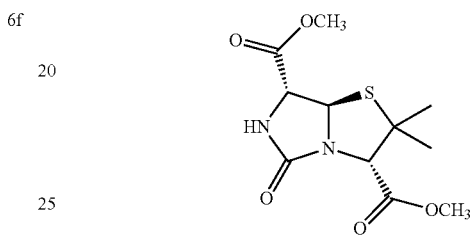

8a

The synthesis of the dimethyl ester was initiated by dissolving the disodium salt 7 (2.0 g, 6.6 mmol) in DMF (50 mL) and methyl iodide (3.0 mL, 48.1 mmol) was added and stirred at room temperature for 12 hours, water was added to the reaction mixture and extracted with (3×100 mL) diethyl ether, dried and concentrated. The crude product was purified by flash silica gel column chromatography using 1:1 EtOAc/hexane as eluent. Pure compound 4a was isolated 1.14 g (60%) as white solid: m.p. 164-166° C.; $^1$H NMR (400 MHz): δ 5.89 (br s, 1H), 5.78 (d, J=1.48 Hz, 1H), 4.70 (s, 1H), 4.35 (d, J=1.52 Hz, 1H), 3.85 (s, 3H), 3.78 (s, 3H), 1.57 (s, 3H), 1.49 (s, 3H); $^{13}$C NMR (100 MHz): δ 170.22, 169.31, 161.24, 70.78, 68.20, 58.63, 58.25, 53.15, 52.05, 33.73, 26.38; HRMS (FAB) m/z calcd for $C_{11}H_{17}N_2O_5S$ [M+H]$^+$289.0788; found 289.0864.

(3S,7R,7aR)-dipropyl 2,2-dimethyl-5-oxohexahy-droimidazo[5,1-b]thiazole-3,7-dicarboxylate (8b)

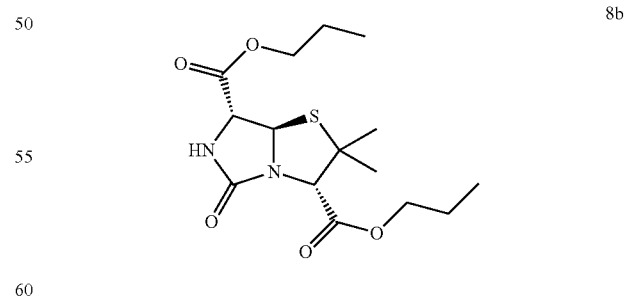

8b

The procedure for the synthesis of 8a was also used for the preparation of 8b. Yield: 62%; m.p. 119-120° C.; $^1$H NMR (400 MHz): δ 6.20 (s, 1H), 5.78 (s, 1H), 4.69 (s, 1H), 4.33 (s, 1H), 4.16 (d, J=6.72 Hz, 2H), 4.10 (dd, J=6.8, 13.5 Hz, 2H), 1.66 (m, 4H), 1.55 (s, 3H), 1.48 (s, 3H), 0.95 (q, J=8.0 Hz, 6H); $^{13}$C NMR (100 MHz): δ 169.90, 168.92, 161.49, 70.80, 68.41, 67.85, 66.91, 58.57, 58.45, 33.95, 26.43, 21.82, 10.48, 10.22; HRMS (FAB) m/z calcd for $C_{15}H_{25}N_2O_5S$ [M+H]$^+$345.1484; found 345.1496.

(3S,7R,7aR)-dibenzyl 2,2-dimethyl-5-oxohexahydroimidazo[5,1-b]thiazole-3,7-dicarboxylate (8c)

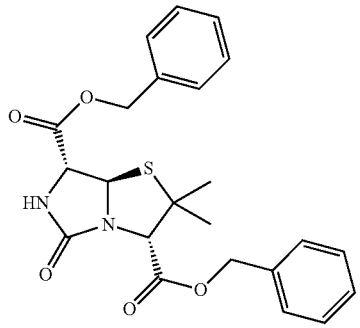

The procedure for the synthesis of 8a was also used for the preparation of 8c. Yield: 63%; m.p. 133-134° C.; $^1$H NMR (400 MHz): δ 7.35-7.28 (m, 10H), 5.95 (s, 1H), 5.83 (d, J=1.4, 1H), 5.22 (m, 2H), 5.17 (s, 2H), 4.74 (s, 1H), 3.37 (d, J=1.36 Hz, 1H), 1.54 (s, 3H), 1.42 (s, 3H); $^{13}$C NMR (100 MHz): δ 169.61, 168.66, 161.28, 134.91, 134.66, 128.76, 128.67, 128.62, 128.49, 70.74, 68.27, 68.03, 67.16, 58.81, 58.42, 33.86, 26.36; HRMS (FAB) m/z calcd for $C_{23}H_{25}N_2O_5S$ [M+H]$^+$441.1484; found 441.1485.

(3S,7R,7aR)-bis(2-(diethylamino)ethyl) 2,2-dimethyl-5-oxohexahydroimidazo[5,1-b]thiazole-3,7-dicarboxylate (8d)

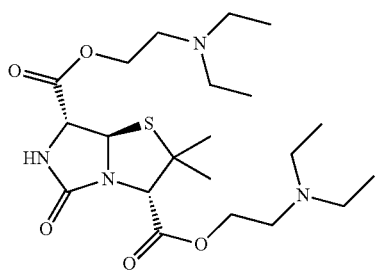

To a suspension of N,N-diethylaminoethyl bromide hydrobromide (1.05 g, 4.0 mmol) in 15 mL of dry DMF was added sodium bicarbonate (1.26 g, 15 mmol). The suspension was stirred at room temperature for 2 hours, then the disodium salt of 8-hydroxypenillic acid 3 (500 mg, 1.6 mmol) was added. The reaction mixture was allowed to stir at room temperature overnight. Water (10 mL) was added to the reaction mixture and extracted with diethyl ether (3×50 mL). The organic layer was dried over $Na_2SO_4$ and concentrated to obtain a colorless semi-solid 8d 189 mg (40%). IR: 3236.26, 3104.39, 2972.52, 2807.69, 1731.15, 1613.18, 1456.81, 1382.74, 1176.99, 1122.12, 1023.36 cm$^{-1}$; $^1$H NMR (400 MHz): δ 6.65 (br s, 1H), 5.73 (d, J=1.48 Hz, 1H), 4.64 (s, 1H), 4.32 (d, J=1.56 Hz, 1H), 4.24 (t, J=5.64 Hz, 2H), 4.17 (t, J=6.4 Hz, 2H), 2.74-2.67 (m, 4H), 2.60-2.51 (m, 8H), 1.53 (s, 3H), 1.47 (s, 3H), 1.02-0.97 (m, 12H); $^{13}$C NMR (100 MHz): δ 169.87, 168.81, 161.52, 70.81, 68.26, 63.98, 58.49, 58.46, 50.98, 50.75, 47.25, 47.21, 33.68, 26.41, 11.85, 11.61; HRMS (FAB) m/z calcd for $C_{21}H_{39}N_4O_5S$ [M+H]$^+$459.2641; found 459.2640.

(3S,7R,7aR)-dimethyl 6-benzyl-2,2-dimethyl-5-oxohexahydroimidazo[5,1-b]thiazole-3,7-dicarboxylate (9a)

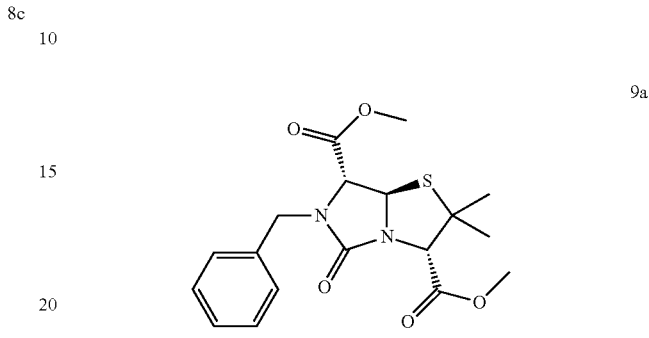

Benzyl bromide (2.05 g, 1.2 mmol) and anhydrous $K_2CO_3$ (2.5 mg, 1.8 mmol) were added to a vigorously stirred solution of 8a (200 mg, 0.7 mmol) in DMF and stirring was continued for 3 hours at 40-45° C. The mixture was then filtered, and the filtrate was diluted with water and extracted with diethyl ether. The extracts were dried over anhydrous $Na_2SO_4$ and the organic solvent was evaporated. The crude product was purified by flash column chromatography EtOAc/hexane (1:2) to obtain white semisolid 9a. Yield: 49%; IR: 2954.09, 1720.97, 1418.49, 1369.85, 1206.99 cm$^{-1}$; $^1$H NMR (400 MHz): δ 7.36-7.25 (m, 5H), 5.63 (d, J=1.2 Hz, 1H), 5.06 (d, J=15.2 Hz, 1H), 4.83 (s, 1H), 4.21 (d, J=15.2 Hz, 1H), 4.08 (d, J=1.3 Hz, 1H), 1.57 (s, 3H), 1.49 (s, 3H); $^{13}$C NMR (100 MHz): δ 169.61, 169.48, 160.13, 135.31, 128.80, 129.22, 127.94, 71.30, 67.01, 60.61, 58.25, 52.86, 52.01, 46.28, 33.86, 26.63; HRMS (FAB) m/z calcd for $C_{19}H_{22}N_3O_5S_2$ [M+H]$^+$379.1327; found 379.1327.

(3S,7R,7aR)-dimethyl 6-(benzo[d]thiazol-2-ylmethyl)-2,2-dimethyl-5-oxohexahydroimidazo[5,1-b]thiazole-3,7-dicarboxylate (9b)

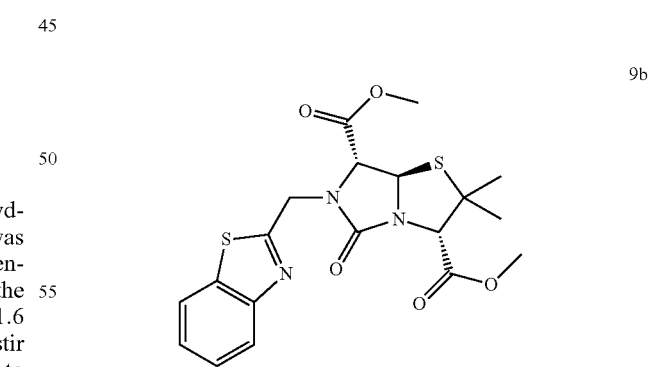

The procedure for the synthesis of 9a was also used for the preparation of 9b. Yield: 40%; $^1$H NMR (400 MHz): δ 7.99 (d, J=8.16 Hz, 1H), 7.89 (d, J=7.96 Hz, 1H), 7.48 (t, J=8.0 Hz, 1H), 7.43 (t, J=8.0 Hz, 1H), 5.71 (d, J=1.6 Hz, 1H), 5.38 (d, J=16.6 Hz, 1H), 4.83 (s, 1H), 4.77 (d, J=16.5 Hz, 1H), 4.51 (d, J=1.68 Hz, 1H), 3.81 (s, 3H), 3.79 (s, 3H), 1.64 (s, 3H), 1.50 (s, 3H); $^{13}$C NMR (100 MHz): δ 169.30, 166.68, 159.74, 152.97, 135.42, 126.28, 125.36, 123.17, 121.89, 71.21, 66.91, 61.48, 58.36, 53.09, 52.11, 44.85, 33.99, 26.67; HRMS (FAB) m/z calcd for $C_{18}H_{23}N_2O_5S$ [M+H]$^+$ 436.1001. found 436.1014.

(6R,7R)-methyl 7-(dimethylamino)-3-methyl-8-oxo-5-thia-1-azabicyclo[4.2.0]oct-2-ene-2-carboxylate (11a)

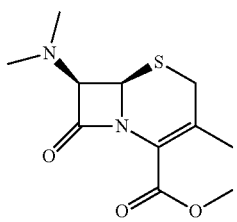

11a

7-ADCA (1.2 g, 4 mmol) was dissolved in 40 mL of water containing 1.68 g (20 mmol, 5 equiv.) of sodium bicarbonate. Carbon dioxide was bubbled through the stirred mixture at room temperature for 12 hours. The concentrated aqueous solution was then lyophilized overnight to yield the yellow powder as a mixture of 10a and 10b. Treatment of the yellow solid mixture with methyl iodide in DMF formed the carboxylate methyl ester 12a as a colorless semisolid. Yield: 15%; $^1$H NMR (400 MHz): δ 4.84 (d, J=4.4 Hz, 1H), 4.03 (d, J=4.5 Hz, 1H), 3.79 (s, 3H), 3.48 (d, J=18.4 Hz, 1H), 3.21 (d, J=18.4 Hz, 1H), 2.48 (s, 5H), 2.13 (s, 3H); $^{13}$C NMR (100 MHz): δ 163.51, 162.85, 130.68, 122.68, 75.42, 57.22, 52.31, 44.75, 30.81, 19.96; HRMS (FAB) m/z calcd for $C_{11}H_{17}N_2O_3S$ [M+H]$^+$257.0960; found 257.0969.

(6R,7R)-benzyl 7-(dibenzylamino)-3-methyl-8-oxo-5-thia-1-azabicyclo[4.2.0]oct-2-ene-2-carboxylate (11b)

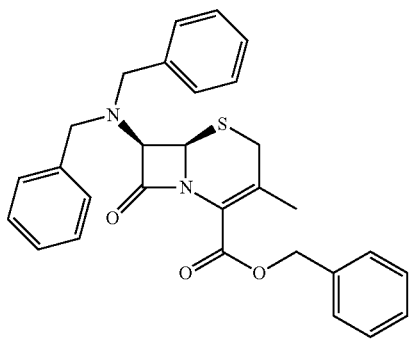

11b

The procedure for the synthesis of 7-ADCA carboxylate methyl-ester 11a was also used for the preparation of 11b. Colorless semi-solid; Yield: 20%; $^1$H NMR (400 MHz): δ 7.46-7.25 (m, 15H), 5.34-5.23 (dd, J=12.2, 33.1 Hz, 2H), 4.77 (d, J=4.6 Hz, 1H), 4.70 (d, J=4.6 Hz, 1H), 4.02-3.92 (dd, J=14.0, 26.0 Hz, 4H), 3.46 (d, J=18.4 Hz, 1H), 3.18 (d, J=18.4 Hz, 1H), 2.10 (s, 3H); $^{13}$C NMR (100 MHz): δ 165.34, 162.36, 138.29, 135.31, 129.14, 129.06, 128.86, 128.71, 128.56, 128.41, 127.29; HRMS (FAB) m/z calcd for $C_{29}H_{29}N_2O_3S$ [M+H]$^+$485.1899; found 485.1902.

(6R,7R)-propyl 3-methyl-8-oxo-7-(propylamino)-5-thia-1-azabicyclo[4.2.0]oct-2-ene-2-carboxylate (11c)

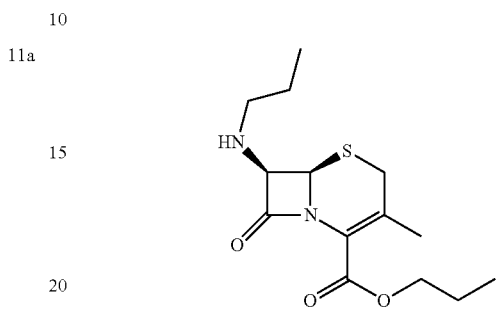

11c

The procedure for the synthesis of 7-ADCA carboxylate methyl-ester 11a was also used for the preparation of 11c. Colorless semisolid; Yield: 15%; $^1$H NMR (400 MHz): δ 4.92 (d, J=4.6 Hz, 1H), 4.56 (d, J=4.5 Hz, 1H), 4.24-4.12 (m, 2H), 3.51 (d, J=18.2 Hz, 1H), 3.19 (d, J=18.2 Hz, 1H), 2.78-2.67 (m, 2H), 2.10 (s, 3H), 1.74-1.69 (m, 2H), 1.55-1.51 (m, 2H), 0.98-0.92 (m, 6H); $^{13}$C NMR (100 MHz): δ 167.39, 162.66, 129.63, 123.04, 69.70, 67.16, 58.37, 51.04, 29.93, 23.57, 21.88, 19.99, 11.52, 10.45; HRMS (FAB) m/z calcd for $C_{14}H_{23}N_2O_3S$ [M+H]$^+$299.1429; found 299.1436.

Sodium (6R,7R)-7-(carboxylatoamino)-3-methyl-8-oxo-5-thia-1-azabicyclo[4.2.0]oct-2-ene-2-carboxylate (10a)

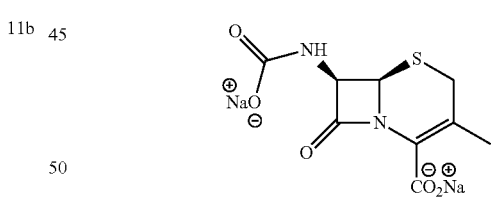

10a

7-ADCA (200 mg, 0.7 mmol) was dissolved in 10 mL of water containing 300 mg (3.5 mmol, 5 equiv.) of sodium bicarbonate. The reaction was carried out in microwave at 70° C. for 2 hours. The concentrated aqueous solution was then lyophilized overnight to obtain the yellow powder 10a. Yield: 99%; m.p.: 218-220° C. (dec.); $^1$H NMR (400 MHz): δ 5.28 (d, J=4.3 Hz, 1H), 4.94 (d, J=4.3 Hz, 1H), 3.11 (d, J=17.9 Hz, 1H), 3.11 (d, J=17.9 Hz, 1H), 1.81 (s, 3H); $^{13}$C NMR (100 MHz): δ 170.36, 169.25, 166.98, 163.03, 160.59, 126.43, 121.69, 61.47, 58.20, 28.16, 18.43; HRMS (FAB) m/z calcd for $C_9H_9N_2Na_2O_5S$ [M+H]$^+$303.0027; found 303.0031.

(6R,7R)-methyl 7-(methoxycarbonylamino)-3-methyl-8-oxo-5-thia-1-azabicyclo[4.2.0]oct-2-ene 2-carboxylate (12a)

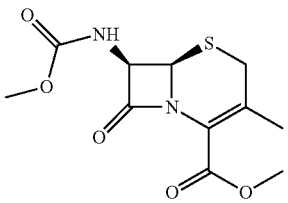

To a suspension of 10a (900 mg, 3 mmol) in DMF (25 mL) was added methyl iodide (0.4 mL, 6 mmol). The reaction mixture was stirred at room temperature for 1 hour. Water was added to the reaction mixture and extracted with diethyl ether (3×50 mL). The organic layer was washed with water and then dried over anhydrous $Na_2SO_4$ and the solvent was removed under reduced pressure. The residue was purified by silica gel column chromatography (1:2 EtOAc/hexane) to yield the complete formation of the methylcarbamate methyl ester 12a, as colorless semisolid. Yield: 20%; $^1$H NMR (400 MHz): δ 5.63-5.60 (m, 1H), 5.41 (d, J=8.6 Hz, 1H), 4.96 (d, J=12.8 Hz, 1H), 3.85 (s, 3H), 3.75 (s, 3H), 3.53 (d, J=18.0 Hz, 1H), 3.24 (d, J=18.2 Hz, 1H), 2.16 (s, 3H); $^{13}$C NMR (100 MHz): δ 162.85, 162.61, 156.11, 130.69, 122.44, 75.41, 57.34, 52.41, 44.73, 30.80, 20.01; HRMS (FAB) m/z calcd for $C_{11}H_{18}N_3O_5S$ [M+H]$^+$ 304.0967; found 304.0990.

(6R,7R)-propyl 3-methyl-8-oxo-7-(methoxycarbonyl amino)-5-thia-1-azabicyclo[4.2.0]oct-2-ene-2-carboxylate (12b).

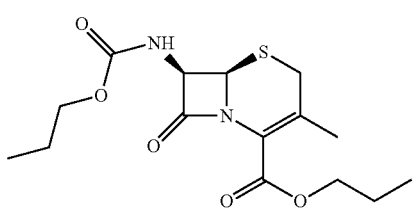

The procedure for the synthesis of methyl-carbamate methyl-ester 12a was also used for the preparation of 12b. Colorless semisolid; Yield: 25%; $^1$H NMR (400 MHz): δ 5.60 (d, J=4.2 Hz, 1H), 5.55 (d, J=9.4 Hz, 1H), 4.97 (d, J=4.4 Hz, 1H), 4.23-4.14 (m, 2H), 4.10-4.05 (m, 2H), 3.52 (d, J=18.2 Hz, 1H), 3.23 (d, J=18.2 Hz, 1H), 2.14 (s, 3H), 1.71-1.54 (m, 4H), 0.96-0.92 (m, 6H); $^{13}$C NMR (100 MHz): δ 163.71, 161.29, 154.77, 129.86, 121.71, 66.18, 59.88, 56.24, 51.96, 28.89, 26.79, 21.22, 21.15, 19.04, 10.51, 9.45; HRMS (FAB) m/z calcd for $C_{15}H_{23}N_2O_5S$ [M+H]$^+$343.1327; found 343.1338.

(6R,7R)-benzyl 7-(benzyloxycarbonylamino)-3-methyl-8-oxo-5-thia-1-azabicyclo[4.2.0]oct-2-ene-2-carboxylate (12c)

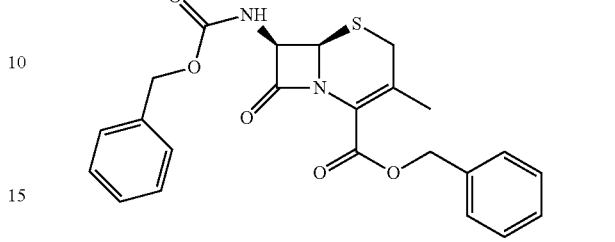

The procedure for the synthesis of methyl-carbamate methyl-ester 12a was also used for the preparation of 12c. Colorless semisolid; Yield: 49%; $^1$H NMR (400 MHz): δ 7.42-7.35 (m, 10H), 5.62 (d, J=4.5 Hz, 1H), 5.56 (d, J=9.6 Hz, 1H), 5.27 (s, 2H), 5.16 (s, 2H), 4.96 (d, J=4.6 Hz, 1H), 3.52 (d, J=18.5 Hz, 1H), 3.22 (d, J=18.5 Hz, 1H), 2.15 (s, 3H); $^{13}$C NMR (100 MHz): δ 164.64, 162.05, 155.47, 135.66, 135.12, 131.87, 128.80, 128.69, 128.63, 128.59, 128.48, 128.44, 128.25, 122.46, 67.80, 67.64, 60.98, 57.24, 30.16, 20.13; HRMS (FAB) m/z calcd for $C_{23}H_{23}N_2O_5S$ [M+H]$^+$439.1327; found 439.1336.

(6R,7R)-benzo[c][1,2,5]thiadiazol-5-ylmethyl 7 ((benzo[c][1,2,5]thiazol-5-ylmethoxy)carbonylamino)-3-methyl-8-oxo-5-thia-1-azabicyclo [4.2.0]oct-2-ene-2-carboxylate (12d)

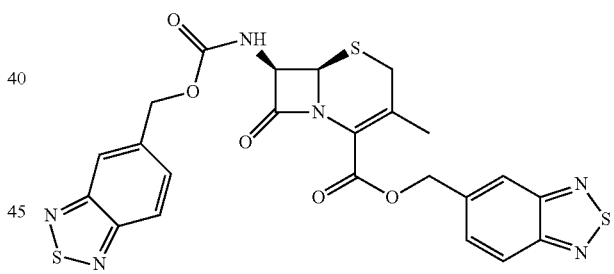

The procedure for the synthesis of methyl-carbamate methyl-ester 12a was also used for the preparation of 12d. Yellow semisolid; Yield: 66%; $^1$H NMR (400 MHz): δ 8.04 (d, J=6.8 Hz, 2H), 8.00 (d, J=4.2 Hz, 2H), 7.67 (dd, J=1.64, 9.04 Hz, 1H), 7.59 (dd, J=1.64, 9.04 Hz, 1H), 5.65 (d, J=4.6 Hz, 1H), 5.62 (d, J=9.6 Hz, 1H), 5.45 (d, J=2.6 Hz, 2H), 5.35 (s, 2H), 5.02 (d, J=4.6 Hz, 1H), 3.56 (d, J=18.5 Hz, 1H), 3.29 (d, J=18.5 Hz, 1H), 2.21 (s, 3H); $^{13}$C NMR (100 MHz): δ 163.53, 160.71, 154.17, 153.46, 136.53, 135.59, 131.93, 128.85, 128.26, 121.02, 120.79, 119.74, 118.97, 106.60, 105.33, 66.64, 66.14, 65.78, 59.95, 56.16, 48.39, 29.21, 29.50, 22.88, 19.22; HRMS (FAB) m/z calcd for $C_{25}H_{21}N_4O_5S_3$ [M+H]$^+$553.0674; found 553.0680.

EXAMPLE 2

High-Throughput Screening Assay

A high-throughput screen was designed to identify compounds that killed *M. tuberculosis*. This screen used a novel model of non-replication that combined four physiological stresses, including hypoxia (1% $O_2$), mild acid (pH 5.0), a flux of nitric oxide and reactive nitrogen intermediates (0.5 mM $NaNO_2$). See Gold, et al. (2012) *Proc. Natl. Acad. Sci. USA* 109:16004-16011. In addition, the assay included replacing a sugar carbon source (glycerol and dextrose) with a fatty acid (50 μM butyrate).

Three lead compounds were identified in the first round of high throughput screening (700 compounds), which had minimal inhibitory concentrations (MIC) of 0.4-0.8 μg/mL after a six day exposure to drug ($NR_{d6}$) in the model of non-replication at pH 5.0, and $LD_{50}$'s of 100 to >100 μg/mL against HepG2 cells (a 2 day exposure). These three compounds were compounds 11c, 12b and 13.

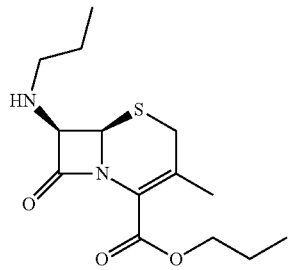

11c

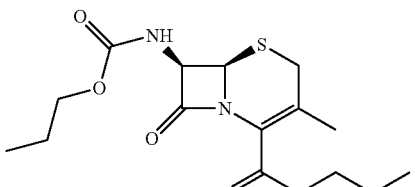

12b

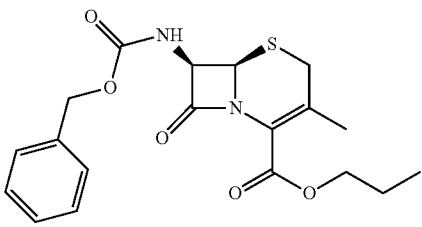

13

These compounds either had very weak activity under replication conditions (i.e., an MIC of 100 μg/mL), or no activity in replication conditions (i.e., >100 μg/mL). The selectivity indices ($LD_{50}/MIC\text{-}NR_{d6}$) ranged from 129 (11c) to >256 (12b and 13). Compound 11c was unstable in the non-replication medium containing 0.5 mM $NaNO_2$, yet still had potent non-replication activity, indicating very fast binding to its target before degradation.

A larger library was also screened (3000+ compounds library) and compounds 11c, 12b and 13 were again identified as exhibiting inhibiting activity. The three compounds were subsequently subjected to cherry pick confirmation. The results of this analysis are presented in Table 1.

TABLE 1

| Structure | % Inhibition | | |
|---|---|---|---|
| | R Screen | NR Screen, Day 7 | NR Screen, Day 10 |
| 13 | 20 | 70 | 36 |
| 12b | 27 | 50 | 23 |

TABLE 1-continued
| Structure | % Inhibition | | |
|---|---|---|---|
| | R Screen | NR Screen, Day 7 | NR Screen, Day 10 |
| 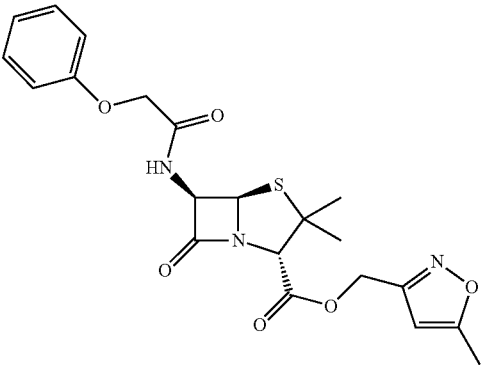 5f | 20 | 38 | 23 |
| 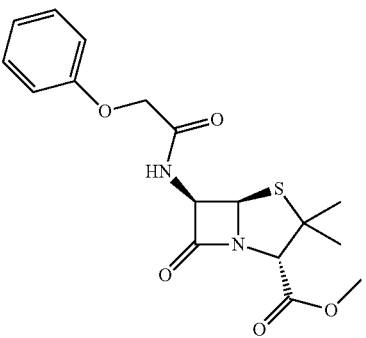 5a | 25 | 35 | 24 |
| 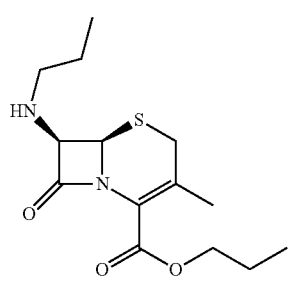 11c | −4 | 21 | 14 |
| 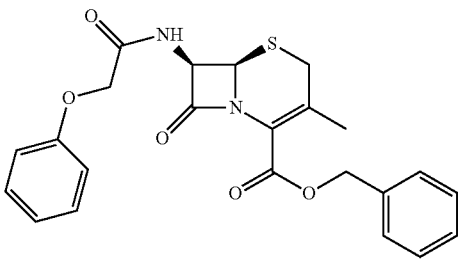 14 | −1 | 21 | 13 |

TABLE 1-continued

| Structure | % Inhibition | | |
|---|---|---|---|
| | R Screen | NR Screen, Day 7 | NR Screen, Day 10 |
| 5h | 8 | 14 | 13 |
| 12c | 2 | 10 | 13 |
| 5j | 8 | 9 | 4 |
| 5c | 21 | 7 | 11 |

TABLE 1-continued
| Structure | % Inhibition | | |
|---|---|---|---|
| | R Screen | NR Screen, Day 7 | NR Screen, Day 10 |
| 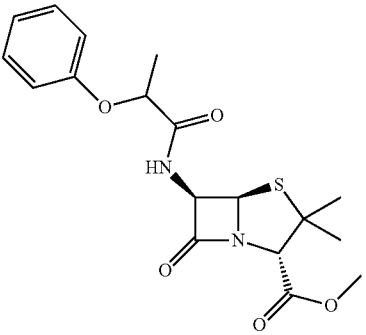 5i | 19 | 7 | 6 |
| 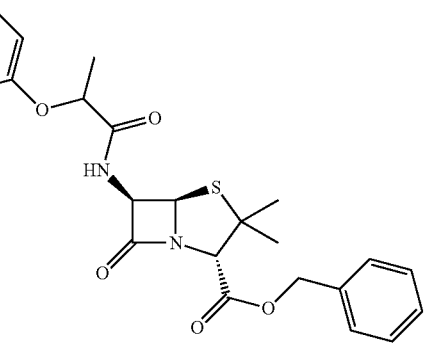 5k | 4 | 2 | 3 |
| 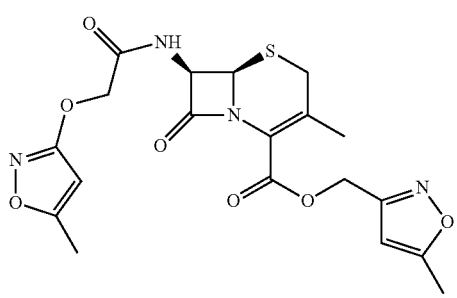 15 | 10 | 1 | 4 |
| 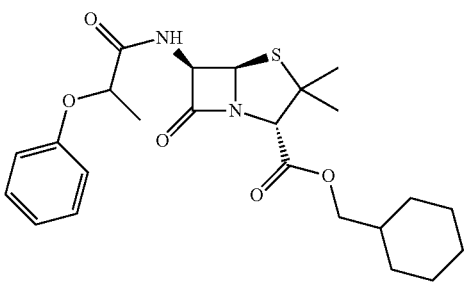 16 | 14 | 0 | 5 |

TABLE 1-continued
| Structure | R Screen | % Inhibition NR Screen, Day 7 | NR Screen, Day 10 |
|---|---|---|---|
| 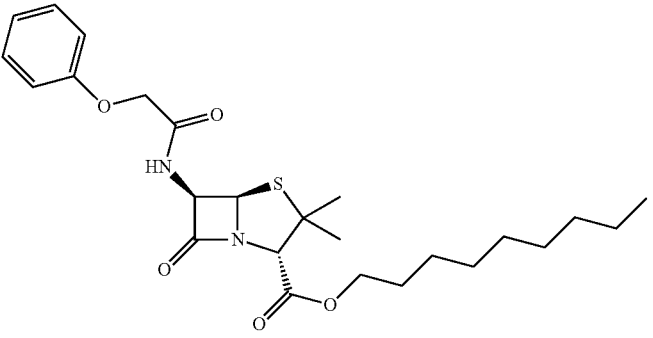  5b | 3 | 0 | 3 |
| 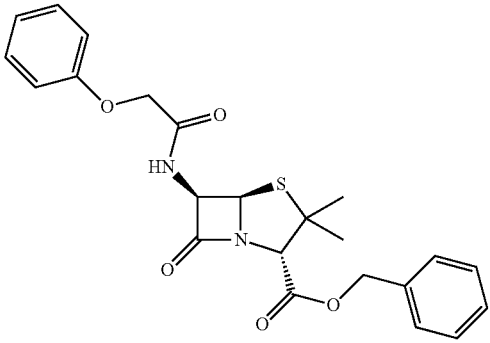  5d | 13 | −5 | 2 |
| 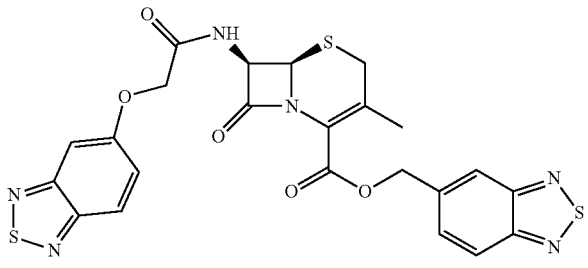  12d | 10 | −11 | 0 |
| 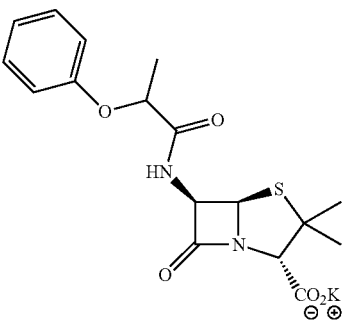  4a | 28 | −24 | −10 |
NR, non-replication; R, replicating.
NR activity in bold indicates compounds with notable activity.

In, addition, compounds 11c, 12b and 13, were subjected to concentration-response curve analysis (dose-response from 0.4-100 μg/mL with 2-fold increments) in both replication and non-replication (NR, pH 5.0 and 5.5 with a 3- or 6-day exposure to drug) conditions. Furthermore, $LD_{50}$ values were determined using a human hepatoma cell line (HepG2) using intracellular ATP levels as a measurement that correlated with cellular viability. The results of these analyses are presented in Table 2 and show that activity was enhanced with an extended time of bacterial exposure to compound.

TABLE 2

| Compound | MIC NR pH 5.0; day 3 exposure (μg/mL) | MIC NR pH 5.0; day 6 exposure (μg/mL) |
|---|---|---|
| 11c | 6.3 | 1.6 |
| 12b | 12.5 | 0.78 |
| 13 | 6.3 | <0.39 |

Given the history of β-lactam degradation during storage and freeze-thaw cycles, the purity of the three cephalosporins was tested and found to be approximately 75%. All three compounds were subsequently resynthesized to >95% purity and analyzed. The results of this analysis are presented in Table 3, which also summarizes LC-MS determination of compound stability in the non-replication media over 6 days.

TABLE 3

| Cmpd | MIC NR pH 5; D3 exposure (μg/mL) | MIC NR pH 5; D6 exposure (μg/mL) | MIC pH 6.6, R cells (μg/mL) | HepG2 toxicity (μg/mL) | Stability |
|---|---|---|---|---|---|
| 11c | 1.6 | 0.4 | >100 | >100 | unstable |
| 12b | 3.1 | 0.4 | 100 | >100 | stable |
| 13 | 1.6 | 0.8 | >100 | 100 | stable |

NR, non-replication; R, replicating; D, day. Stability analysis was carried out in non-replication media without bovine serum albumin and tyloxapol.

The three cephalosporins were then tested against a variety of Gram positive and negative bacteria to determine the antibiotic spectrum (Table 4; n=1 experiment).

TABLE 4

| Bacterium | Gram status | 11c | 12b | 13 |
|---|---|---|---|---|
| Escherichia coli | negative | >100 μg/mL | >100 μg/mL | >100 μg/mL |
| Streptococcus | positive | >100 μg/mL | >100 μg/mL | >100 μg/mL |
| Pseudomonas aeruginosa | negative | >100 μg/mL | >100 μg/mL | >100 μg/mL |
| Staphylococcus aureus | positive | >100 μg/mL | >100 μg/mL | >100 μg/mL |

None of the compounds displayed any activity on other organisms, indicating specificity of these compounds for *M. tuberculosis*. Furthermore, it was demonstrated that the cephalosporin activity in the non-replication model was dependent on nitrite.

EXAMPLE 3

Probe Compound Library Based Upon β-Lactam Chemistry

The acylation of 6-APA at its NH moiety was carried out herein. Penicillin 4a (penicillin V) described in Scheme 1 were prepared by treating phenoxyacetyl chloride with 6-aminopenicillanic acid (6-APA) in aqueous acetone solution containing an excess of sodium bicarbonate. The penicillin as the free acid (pH=2) was extracted into a water-immiscible organic solvent and then precipitated as the potassium salt by the addition of potassium 2-ethylhexanoate. The compound obtained by this method was found to be easier to purify and in good yield (80%). The potassium salt was washed with dry acetone immediately after filtration, no further recrystallization was necessary since the material obtained was found to be analytically pure. The racemic phenoxypropanyl chloride was used in the preparation of compound 4b, so the new penicillin 4b was obtained as a mixture of diastereoisomers.

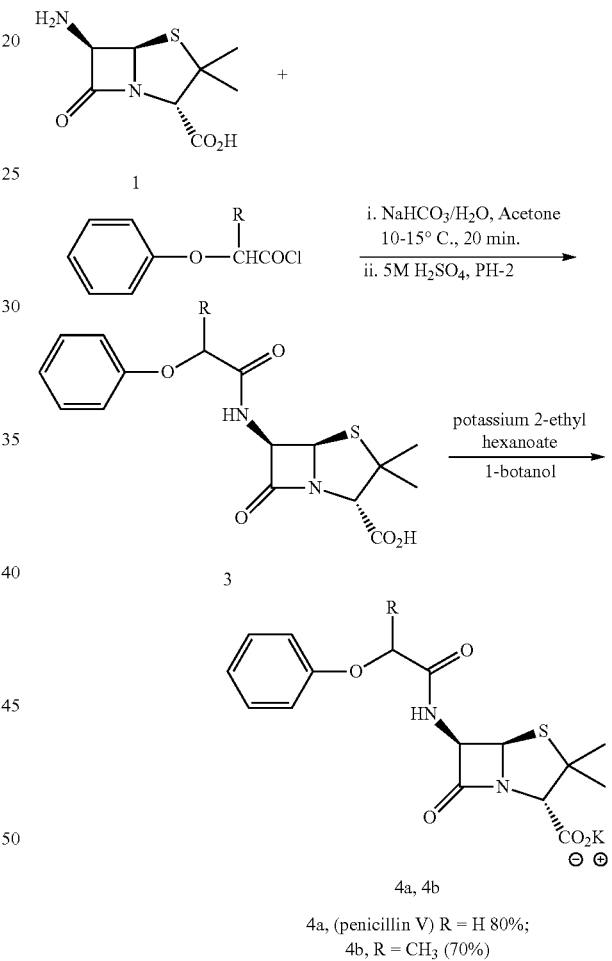

SCHEME 1

Parallel synthesis of carboxylic acid esters of 6-APA was employed to react various aliphatic, aromatic and heterocyclic bromide or iodide with the potassium salt of penicillins (4a and 4b) to generate penicillin carboxylic esters 5a-5k (Scheme 2) in good to modest yields. The penicillin esters were isolated by flash chromatography over silica gel using 9:1 EtOAc/hexane as an eluent. The final products were characterized by $^{1}$H NMR, $^{13}$C NMR, LC-MS and HRMS.

SCHEME 2

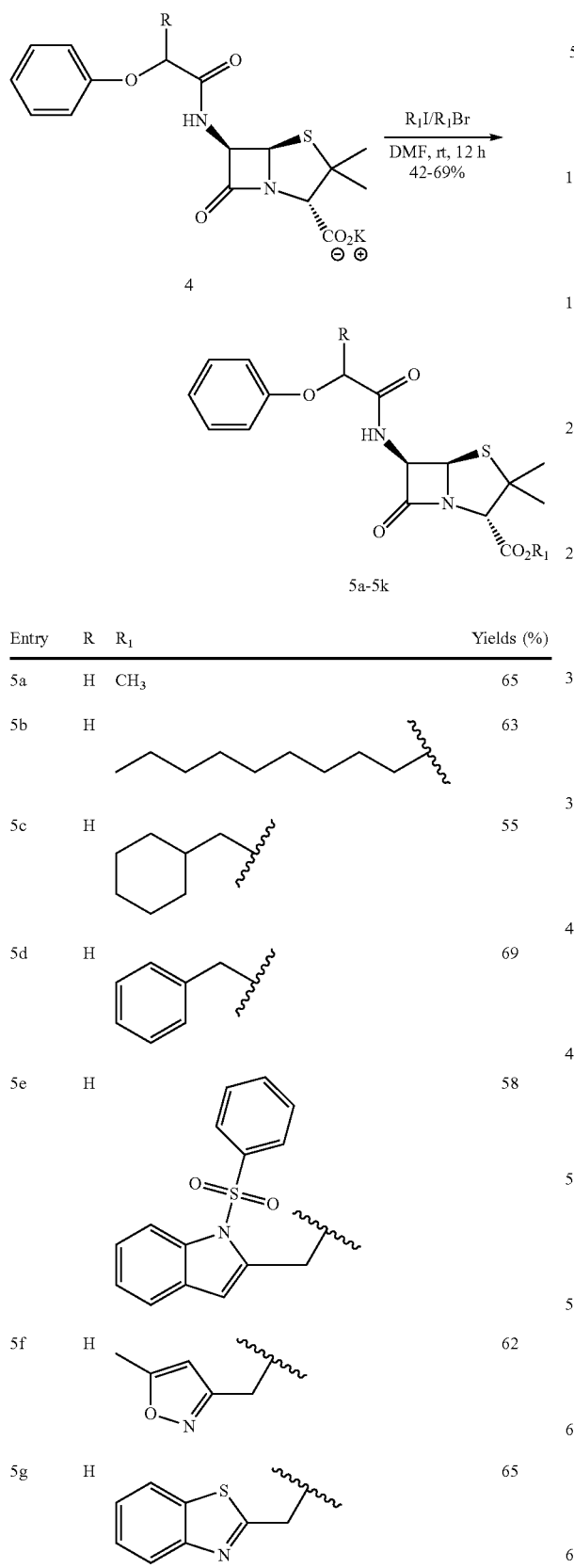

SCHEME 2 -continued

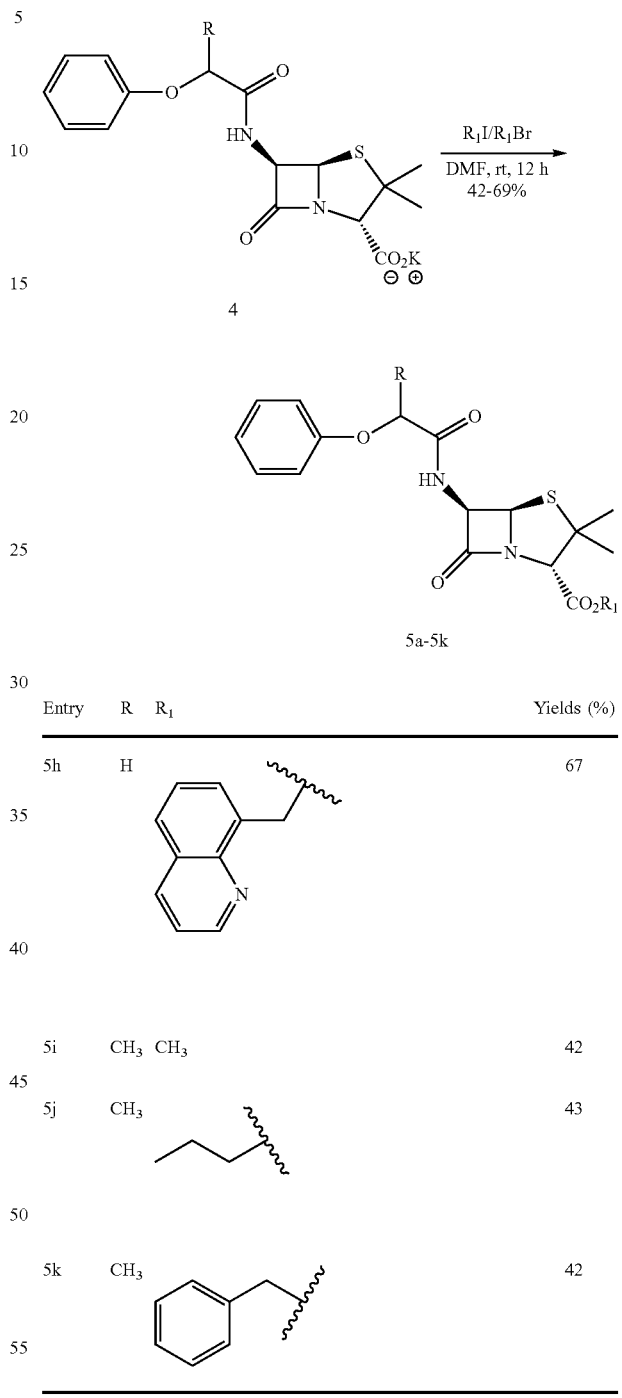

Nucleophilic ring opening of β-lactams from methyl ester of penicillin V with various aromatic, aliphatic and heterocyclic amines, as shown in Scheme 3, was achieved at room temperature over 12 hours to afford compounds 6a-6f in modest yields. The target thiazolidine amides were isolated by flash chromatography over silica gel using 1:1 EtOAc/hexane as an eluent. The yields reported are isolated yields and the purity of the final products was confirmed using $^1$H NMR, $^{13}$C NMR, LC-MS and HRMS.

SCHEME 3

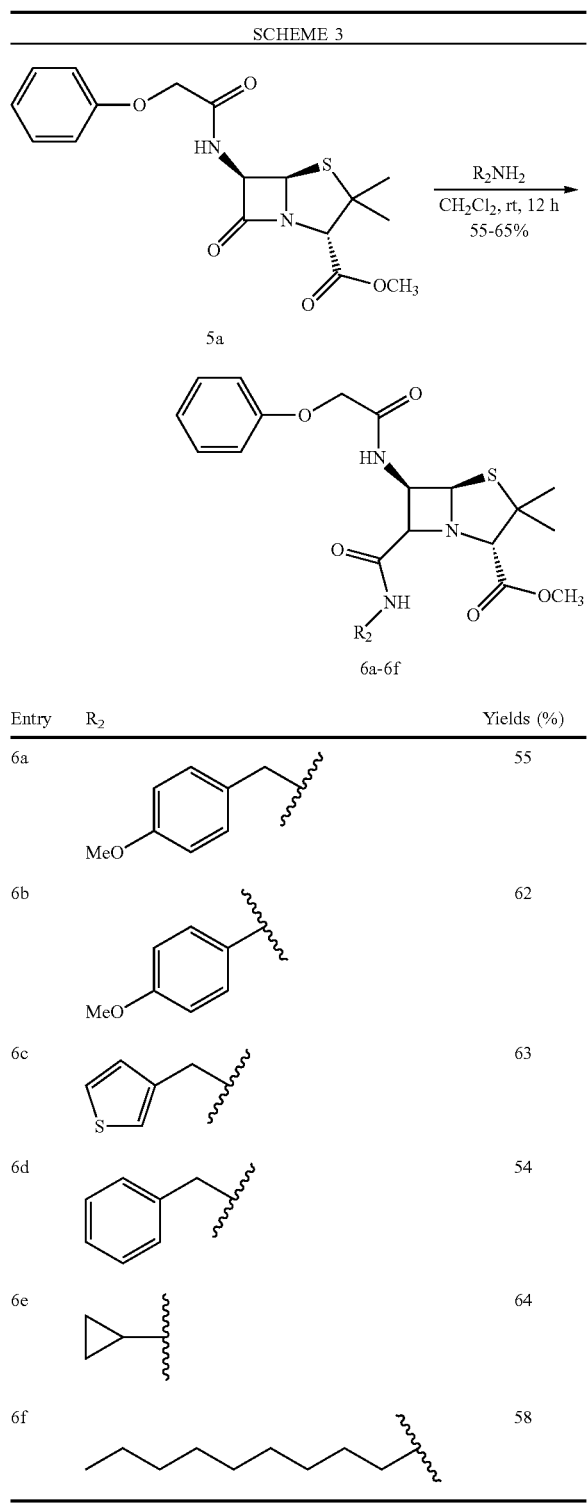

| Entry | R₂ | Yields (%) |
|---|---|---|
| 6a | 4-MeO-C₆H₄-CH₂- | 55 |
| 6b | 4-MeO-C₆H₄-(CH₂)₂- | 62 |
| 6c | 3-thienyl-CH₂- | 63 |
| 6d | C₆H₅-CH₂- | 54 |
| 6e | cyclopropyl- | 64 |
| 6f | n-decyl- | 58 |

The rearrangement of the β-lactam ring was also investigated. Thus, synthesis of disodium salt of 8-hydroxypenillic acid from 6-APA, as shown in Scheme 4, was carried out by modification of a known method (Johnson & Hardcastle (1961) supra). 6-APA (4.5 g) was dissolved in 100 mL of water containing 3.5 g (2 equiv.) of sodium bicarbonate. Carbon dioxide from dry ice source was bubbled through the stirred mixture at room temperature for 24 hours. The concentrated aqueous solution was then lyophilized overnight to produce the disodium salt of the required product as a pale yellow powder in high yield (90%), m.p. 228-230° C. (dec.).

SCHEME 4

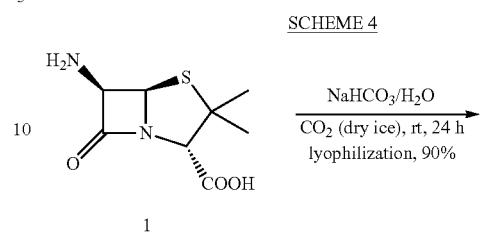

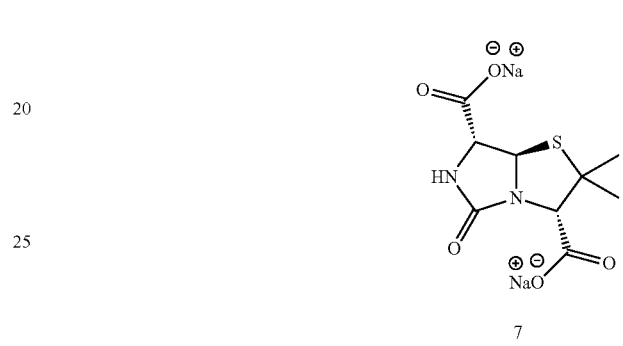

Although 8-hydroxypenillic acid is the traditional common name for this compound it likely exists predominantly in the keto form as depicted in 7. The mechanism proposed for the reaction is also shown in Scheme 5. Thus, it appears that the compound is formed by carboxylation of the amino group of 6-aminopenicillanic acid followed by a penillic acid rearrangement.

SCHEME 5

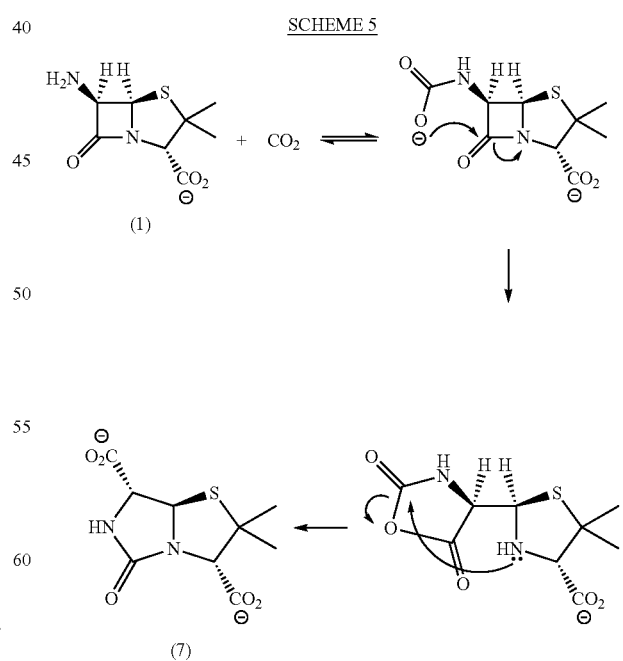

Spectral analysis of the $^1$H and $^{13}$C NMR features of 8-hydroxypenillic acid (isolated as the disodium salt by lyophilization) was consistent with the fused imidazolinethiazolidine structure 7. Chemical shifts of the 3- and 6-carbonyl carbons (~170 ppm) gave evidence of the ionized state of both carboxylate functions. The $^1$H NMR spectrum of the disodium salt of 8-hydroxypenillic acid was well resolved and displayed no unassigned signals of significant intensity, evidence that the conversion of 1 to 7 proceeds in a highly stereo-specific manner.

Alkylation of 8-hydroxypenillic acid was initiated by using aliphatic and aromatic bromides, which were reacted with the disodium salt 7 in DMF to afford the corresponding di-ester analogues 8a-8c as white solids (Scheme 6). Since N,N-diethylaminoethyl bromide hydrobromide was employed for the synthesis of 8d, excess sodium bicarbonate was added first into the solution as an exceptional to quench the hydrobromide acid. The compound 8d was isolated by extracting with diethyl ether from the water solution of the reaction mixture.

The second diversification of 8-hydroxypenillic acid was carried out at its $N^6$ position by alkylation with benzyl bromide and 2-(bromomethyl)benzo[d]thiazole using potassium carbonate as base in DMF (Scheme 7).

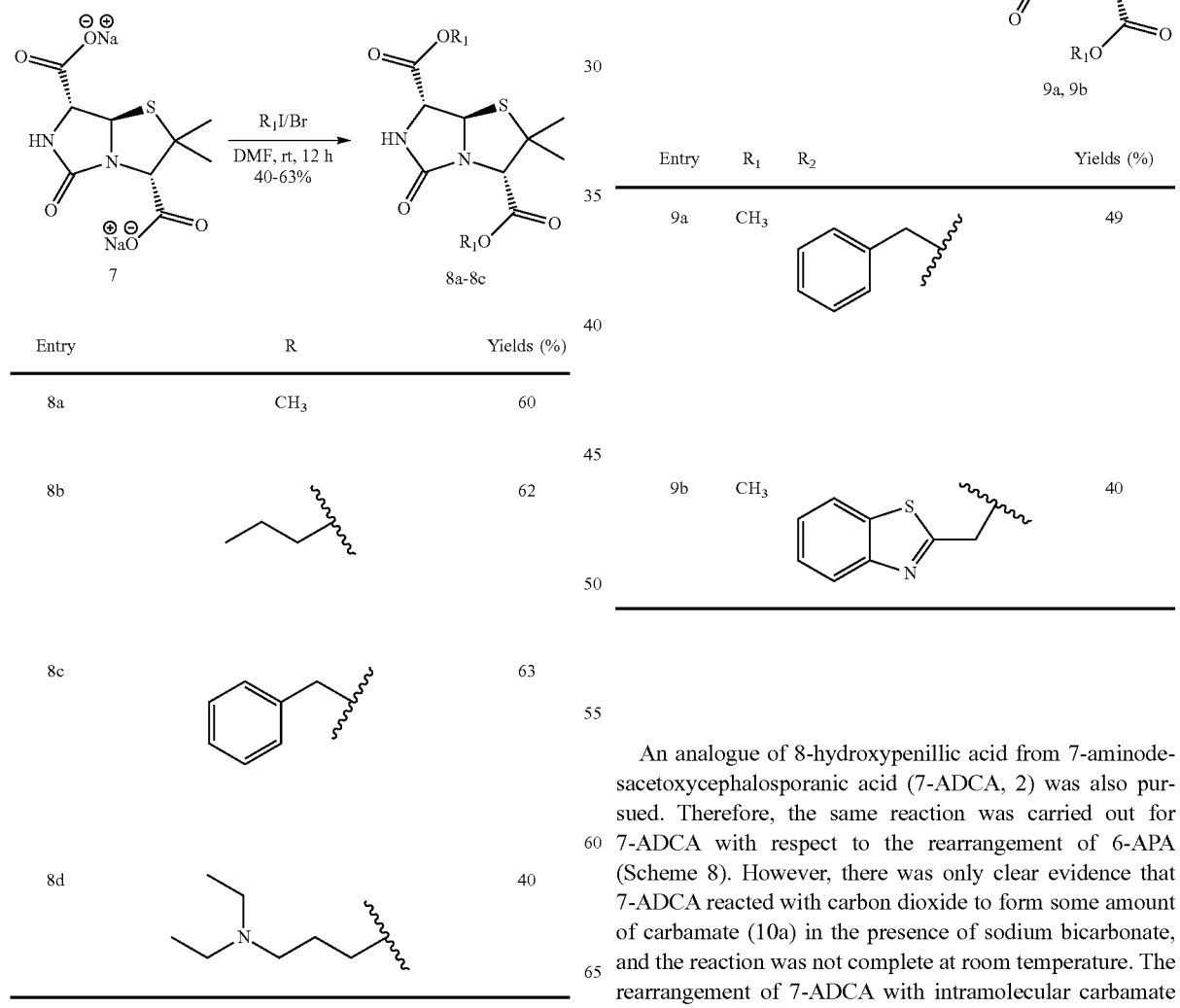

An analogue of 8-hydroxypenillic acid from 7-aminodesacetoxycephalosporanic acid (7-ADCA, 2) was also pursued. Therefore, the same reaction was carried out for 7-ADCA with respect to the rearrangement of 6-APA (Scheme 8). However, there was only clear evidence that 7-ADCA reacted with carbon dioxide to form some amount of carbamate (10a) in the presence of sodium bicarbonate, and the reaction was not complete at room temperature. The rearrangement of 7-ADCA with intramolecular carbamate participation was less facile than 6-APA.

SCHEME 8

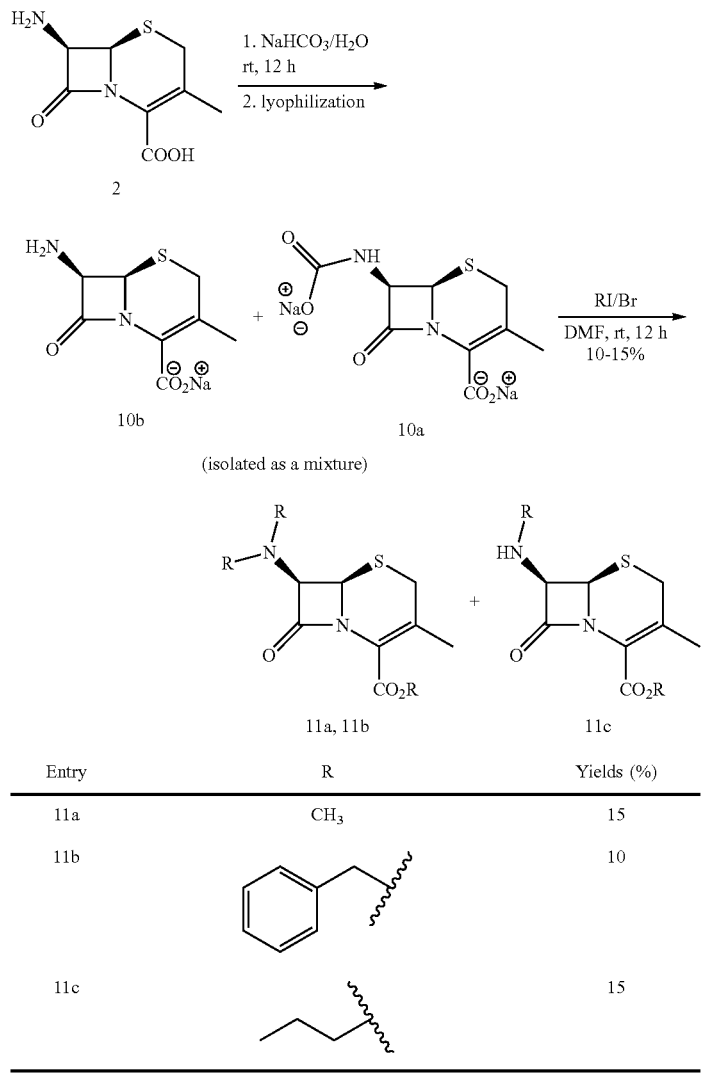

| Entry | R | Yields (%) |
|---|---|---|
| 11a | CH₃ | 15 |
| 11b | (benzyl) | 10 |
| 11c | (butyl) | 15 |

The carbamate formation with 7-ADCA was completed by using microwave synthesizer at 70° C. for two hours. Direct chemical verification of complete carbamate formation involved the preparation of carbamate esters (12a-12d) by treatment of the solid obtained from a lyophilized bicarbonate solution of 7-ADCA after microwave condition with various aliphatic, aromatic and heterocyclic bromides (Scheme 9).

SCHEME 9

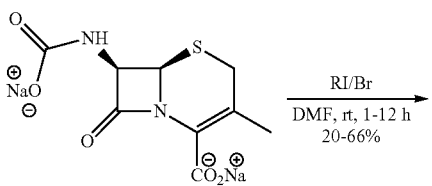

-continued

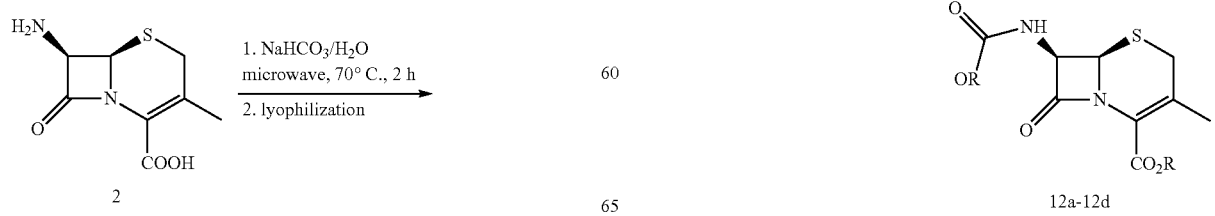

49 -continued

| Entry | R | Yields (%) |
|---|---|---|
| 12a | CH₃ | 20 |
| 12b | (n-butyl) | 25 |
| 12c | (benzyl, CH₂Ph) | 49 |

50 -continued

| | | |
|---|---|---|
| 12d | (2,1,3-benzothiadiazol-5-ylmethyl) | 66 |

EXAMPLE 4

Structure Activity Relationship of β-Lactams

Structure-Activity Relationship (SAR) analysis of β-lactams is presented in Tables 5-7. Compounds 17-107 exhibit inhibitory activity in one or both of the replication or non-replication mycobacterial model (Table 8). Moreover, compounds focusing on log P are expected to exhibit enhanced uptake through the thick, waxy Mycobacterial cell wall.

TABLE 5

| $R_2$ | $R_1$ = —O-n-butyl | $R_1$ = —O-n-propyl | $R_1$ = —O-ethyl |
|---|---|---|---|
| —CH₂Ph | 17 | 18 | 19 |
| —CH₃ (with stereo) | 20 | 21 | 22 |
| —CH₂CH₂CH₃ | 23 | 11c | 24 |
| —(CH₂)₄CH₃ | 25 | 26 | 27 |
| —CH₂CH(CH₃)₂ (isobutyl-like) | 28 | 29 | 30 |
| —CH₂C(O)O-n-propyl | 31 | 12b | 32 |
| —CH₂C(O)CH₂C≡CH | 33 | 34 | 35 |

TABLE 5-continued
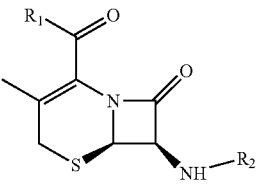
| | R₁ | | |
|---|---|---|---|
| |  |  | 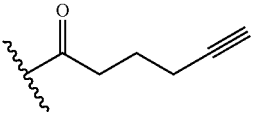 [SMILES: *C(=O)CCCC#C] |
| R₂ | | | |
| 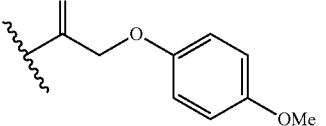 | 36 | 37 | 38 |
| 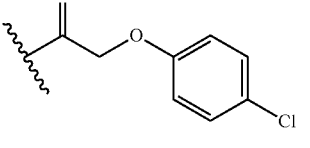 | 39 | 13 | 40 |
| 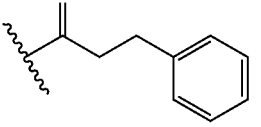 | 41 | 42 | 43 |
| 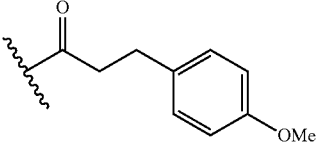 [SMILES: *C(=O)CCc1ccc(OC)cc1] | 44 | 45 | 46 |
| 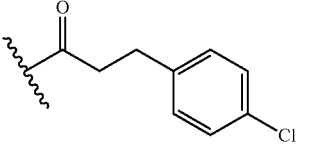 | 47 | 48 | 49 |
|  | 50 | 51 | 52 |
|  | 53 | 54 | 55 |

TABLE 6
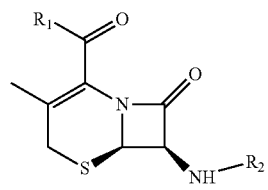
| R2 | R1 -O-CH3 | R1 -O-CH2-(3-methylisoxazol-5-yl) | R1 -O-CH2-C≡CH |
|---|---|---|---|
| Ph (benzyl) | 56 | 57 | 58 |
| CH3 | 59 | 60 | 61 |
| propyl | 62 | 63 | 64 |
| pentyl | 65 | 66 | 67 |
| isobutyl | 68 | 69 | 70 |
| propyl ester | 71 | 72 | 73 |
| CH2C(O)CH2C≡CH | 74 | 75 | 76 |
| (CH2)3C≡CH ketone | 77 | 78 | 79 |
| CH2C(O)CH2OPh | 80 | 81 | 82 |
| CH2C(O)CH2O-C6H4-OMe | 83 | 84 | 85 |

TABLE 6-continued
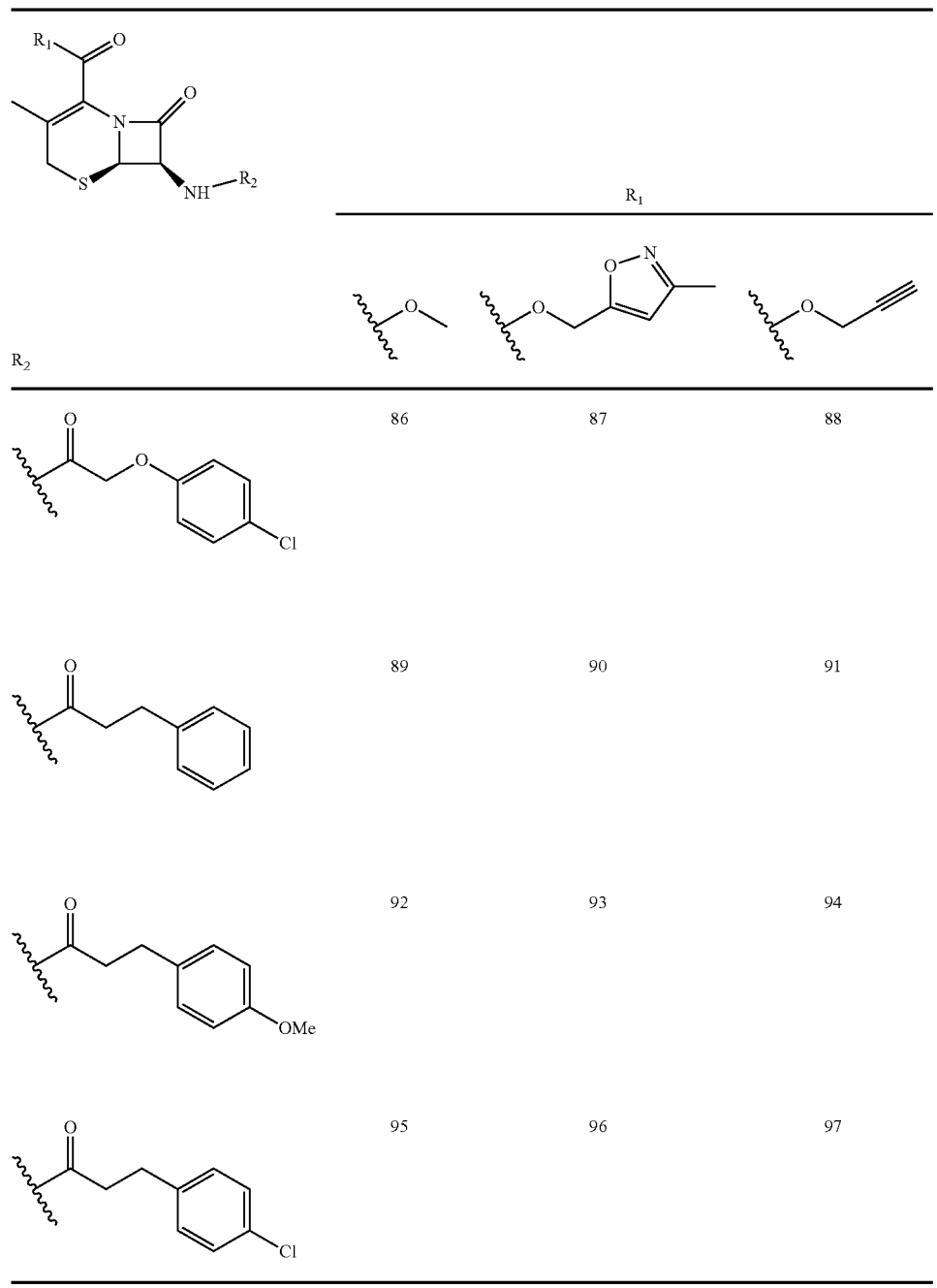
TABLE 7
| Compound | Structure |
|---|---|
| 98 | 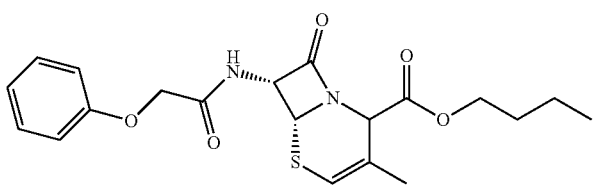 |

TABLE 7-continued
| Compound | Structure |
|---|---|
| 99 | 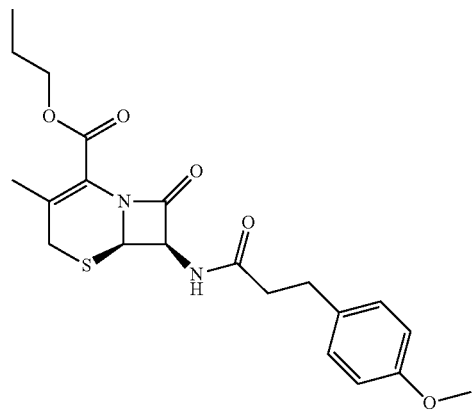 |
| 100 | 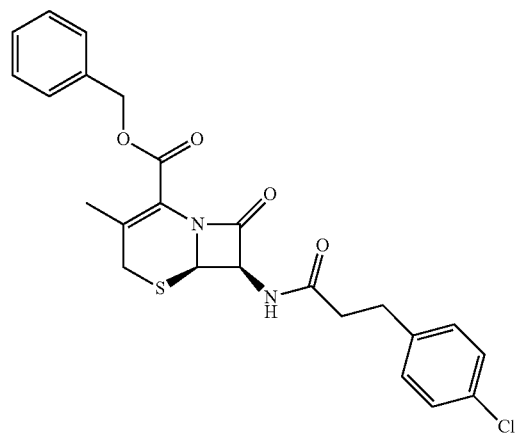 [SMILES: CC1=C(C(=O)OCc2ccccc2)N2C(=O)[C@@H](NC(=O)CCc3ccc(Cl)cc3)[C@H]2SC1] |
| 101 | 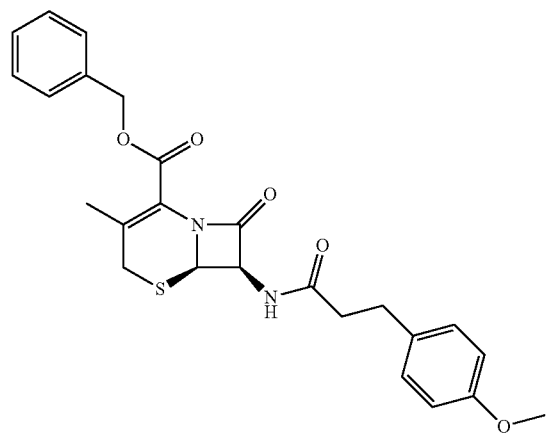 [SMILES: COc1ccc(CCC(=O)N[C@@H]2C(=O)N3C(C(=O)OCc4ccccc4)=C(C)CS[C@H]23)cc1] |

TABLE 7-continued
| Compound | Structure |
|---|---|
| 102 | 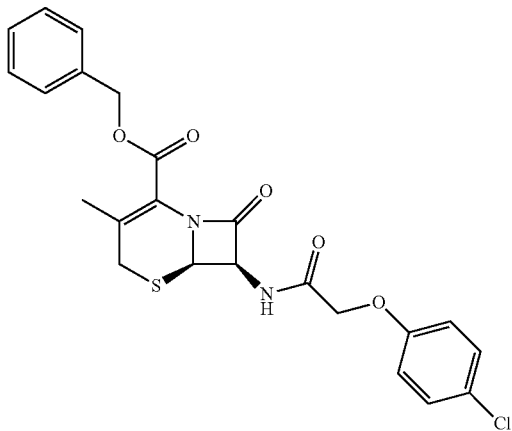 |
| 103 | 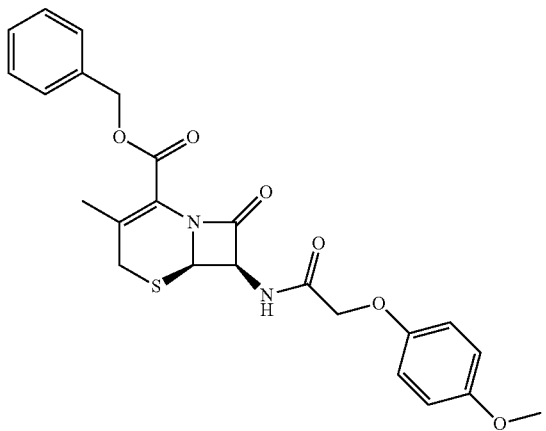 [SMILES: COc1ccc(OCC(=O)N[C@@H]2C(=O)N3C(C(=O)OCc4ccccc4)=C(C)CS[C@H]23)cc1] |
| 104 | 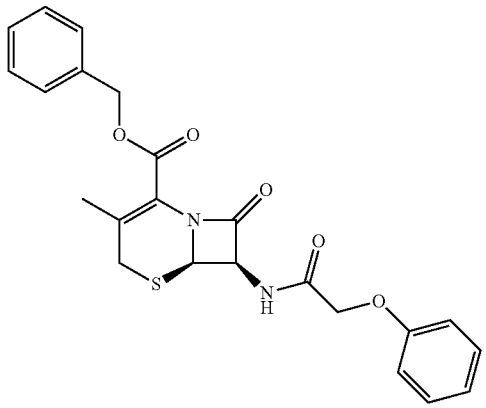 [SMILES: CC1=C(C(=O)OCc2ccccc2)N2C(=O)[C@@H](NC(=O)COc3ccccc3)[C@H]2SC1] |

TABLE 7-continued

| Compound | Structure |
|---|---|
| 105 | 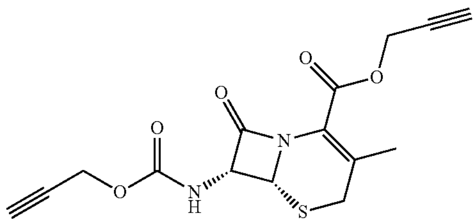 [SMILES: C#CCOC(=O)N[C@@H]1C(=O)N2C(C(=O)OCC#C)=C(C)CS[C@H]12] |
| 106 | 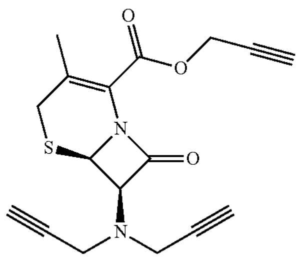 [SMILES: C#CCOC(=O)C1=C(C)CS[C@@H]2[C@H](N(CC#C)CC#C)C(=O)N12] |
| 107 | 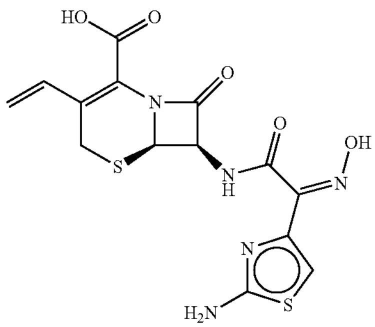 |

TABLE 8

| | MIC NR at 0.01 Inoc. and 3 Day Exposure to Drug | | |
|---|---|---|---|
| Compound | 7 Day Outgrowth (μg/mL) | 11 Day Outgrowth (μg/mL) | HepG2 Toxicity LD$_{50}$ (μg/mL) |
| 13 | 0.2-0.39 | 0.39-0.78 | 100 |
| 34 | 1.56 | 3.13 | >100 |
| 39 | 0.10 | 0.20 | 100 |
| 40 | 0.39 | 0.78 | >100 |
| 42 | 0.20 | 0.39 | >100 |
| 43 | 0.39 | 1.56 | >100 |
| 44 | 0.2 | 0.39 | >100 |
| 45 | 0.39 | 0.39 | 100 |
| 46 | 0.39 | 078 | 50 |
| 47 | 0.20 | 0.39-0.78 | 50->100 |
| 48 | 0.10 | 0.20 | >100 |
| 49 | 0.20 | 0.39 | >100 |
| 50 | 0.10 | 0.20 | >100 |
| 51 | 0.10 | 0.10 | >100 |
| 52 | 0.20 | 0.39 | >100 |
| 53 | 0.20 | 0.39 | >100 |
| 54 | 0.20 | 0.39 | >100 |
| 55 | 0.20 | 0.39 | >100 |
| 80 | 1.56 | 1.56 | >100 |
| 82 | 1.56 | 3.13 | >100 |
| 83 | 1.56 | 1.56 | >100 |
| 85 | 0.78 | 1.56 | >100 |
| 86 | 1.56 | 1.56-3.13 | >100 |
| 88 | 0.78 | 1.56 | 100 |
| 89 | 0.78 | 0.78 | >100 |
| 91 | 0.78 | 1.56 | >100 |
| 92 | 0.39 | 0.78 | >100 |
| 94 | 0.78 | 1.56 | >100 |
| 95 | 0.20 | 0.39 | >100 |
| 97 | 0.39 | 0.78 | 100 |
| 11c | 0.39-0.78 | 0.78 | 100->100 |
| 12b | 1.56 | 1.56-3.13 | >100 |
| 98 | 0.39 | 0.39 | 100 |
| 99 | 0.10 | 0.20 | >100 |
| 100 | 0.39 | 0.78 | 50 |
| 101 | 0.39 | 0.78 | >100 |
| 102 | 0.78 | 1.56 | >100 |
| 103 | 0.78 | 1.56 | >100 |
| 104 | 1.56 | 3.13 | >100 |
| 105 | 6.25 | 12.50 | >100 |
| 106 | 12.50 | 25.00 | 100 |
| 107 | 50.00 | 50.00 | >100 |

Ranges indicated results from multiple assays.

In addition, free acid derivatives were generated (Compounds 108-116), as was an amide (Compound 117), and each was shown to exhibit inhibitory activity (Table 9).

TABLE 9

| Compound | Structure | MIC NR 0.01 Inoc. (μg/ml) | 0.1 Inoc. (μg/ml) | MIC R (μg/ml) | HepG2 LD$_{50}$ (μg/mL) |
|---|---|---|---|---|---|
| 108 | 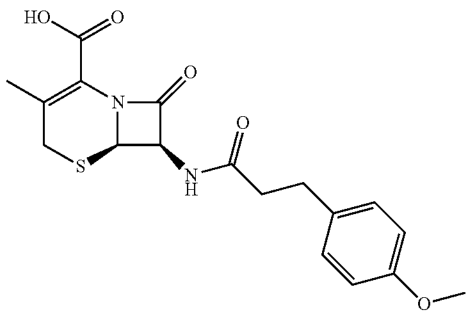 | >100 | >100 | >100 | >100 |
| 109 | 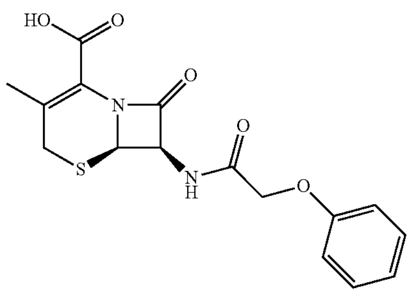 [SMILES: CC1=C(C(=O)O)N2C(=O)[C@@H](NC(=O)COc3ccccc3)[C@H]2SC1] | 100 | >100 | >100 | >100 |
| 110 | 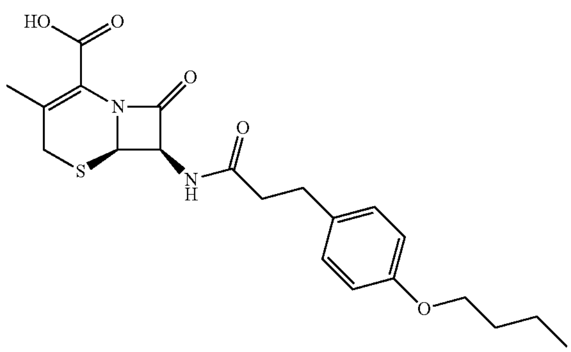 [SMILES: CCCCOc1ccc(CCC(=O)N[C@@H]2C(=O)N3C(C(=O)O)=C(C)CS[C@H]23)cc1] | 100 | >100 | 100 | >100 |
| 111 | 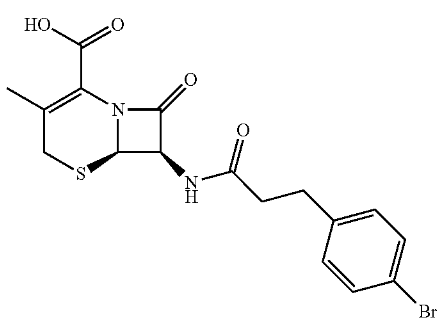 [SMILES: CC1=C(C(=O)O)N2C(=O)[C@@H](NC(=O)CCc3ccc(Br)cc3)[C@H]2SC1] | >100 | >100 | 100 | >100 |
| 112 | 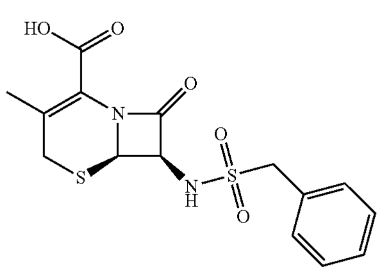 [SMILES: CC1=C(C(=O)O)N2C(=O)[C@@H](NS(=O)(=O)Cc3ccccc3)[C@H]2SC1] | >100 | >100 | >100 | >100 |

TABLE 9-continued

| Compound | Structure | MIC NR 0.01 Inoc. (μg/ml) | MIC NR 0.1 Inoc. (μg/ml) | MIC R (μg/ml) | HepG2 LD$_{50}$ (μg/mL) |
|---|---|---|---|---|---|
| 113 | 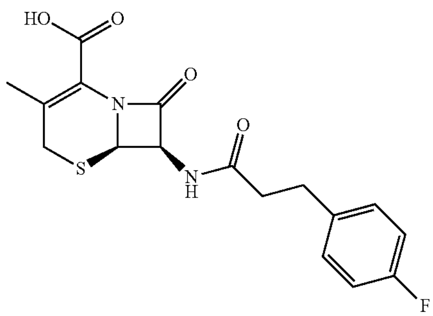 [SMILES: CC1=C(C(=O)O)N2C(=O)[C@@H](NC(=O)CCc3ccc(F)cc3)[C@H]2SC1] | >100 | >100 | 100 | >100 |
| 114 | 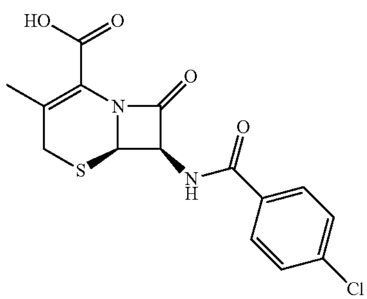 [SMILES: CC1=C(C(=O)O)N2C(=O)[C@@H](NC(=O)c3ccc(Cl)cc3)[C@H]2SC1] | >100 | >100 | >100 | >100 |
| 115 | 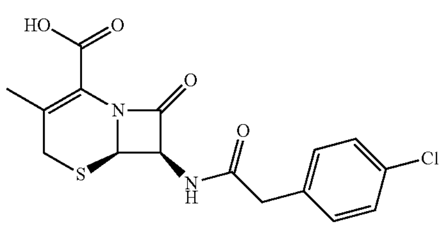 [SMILES: CC1=C(C(=O)O)N2C(=O)[C@@H](NC(=O)Cc3ccc(Cl)cc3)[C@H]2SC1] | >100 | >100 | 100 | >100 |
| 116 | 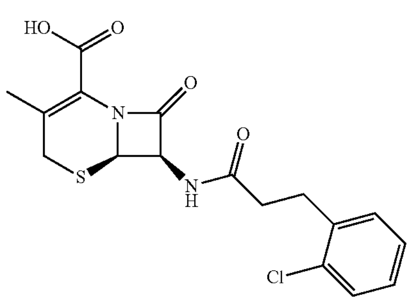 [SMILES: CC1=C(C(=O)O)N2C(=O)[C@@H](NC(=O)CCc3ccccc3Cl)[C@H]2SC1] | >100 | >100 | >100 | >100 |

| | | MIC NR | | | |
|---|---|---|---|---|---|
| Compound | Structure | 0.01 Inoc. (µg/ml) | 0.1 Inoc. (µg/ml) | MIC R (µg/ml) | HepG2 LD$_{50}$ (µg/mL) |
| 117 | | 100 | >100 | >100 | >100 |

*3 Day Exposure to Drug.

EXAMPLE 5

Activity of 3,4-Olefinic Isomers 3,4-Olefinic isomers were also prepared (compounds 118 and 119). Compounds 118 and 119 both had a minimum inhibitory concentration of 3.1 µg/mL against non-replicating M. tuberculosis compared to 100 µg/mL against replicating M. tuberculosis.

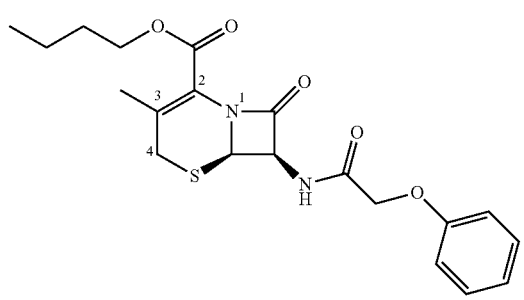

118

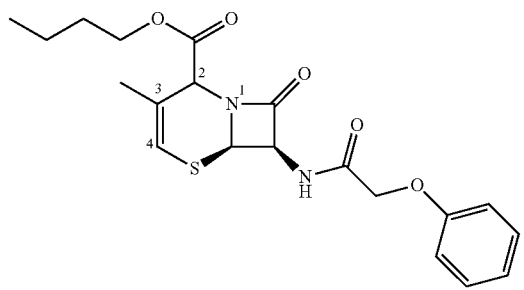

119

Therefore, this invention also includes 3,4-olefinic isomers.

EXAMPLE 6

Non-Replicating Active Cephalosporins Display Inoculum-Dependent Killing

The potency of many cell-wall active antibiotics, including β-lactams, is known to display inoculum dependency. To determine whether this held true for the non-replicating (NR) active cephalosporins, the NR minimal inhibitory concentrations (MICs) of NR-active cephalosporins was determined at inocula of A$_{580}$ of 0.1 and 0.01 using the BSL2+ΔpanCDΔlysA Mycobacterium tuberculosis (Mtb) strain. Although some MICs were not impacted, many of the NR-active cephalosporins gained activity against Mtb at a lower inoculum; in some cases up to a 16-fold decrease in MIC. Moreover, significant cidality of compound 13 was observed against wild-type Mtb at a starting inoculum of 0.01 (FIG. 1). This is consistent with previous findings, which showed that the NR-active cephalosporins kill wild-type Mtb in a CFU-based assay and demonstrates that they gain activity at a lower inoculum. Moreover, this result is consistent with the proposed mechanism of action of cephalosporins, which target peptidoglycan biosynthesis.

EXAMPLE 7

NR-Active Cephalosporins do not Synergize with a β-Lactamase Inhibitor

Meropenem synergizes with clavulanic acid, a β-lactamase inhibitor, to potently kill Mtb (Hugonnet, et al. (2009) Science 323:1215-8). To determine whether the NR-active cephalosporins shared this property, wild-type Mtb was exposed to compound 13 in the presence of absence of clavulanate under NR conditions for 7 days. Bacterial viability was monitored by enumeration of 7H11 agar plates containing OADC supplement. An increase in potency of compound 13 to kill Mtb was not detected in the presence of clavulanate. It was posited that compound 13 failed to kill replicating (R) Mtb due to inactivation by β-lactamases. To test this, the MIC of compound 13 was tested against replicating Mtb in the presence or absence of clavulanic acid. The MICs were identical in the presence or absence of clavulanic acid against replicating Mtb. Thus, these data indicate that compound 13 is not a substrate for clavulanate-inhibitable β-lactamases.

EXAMPLE 8

Compound 13 Kills Intracellular Mtb

Figure 2:
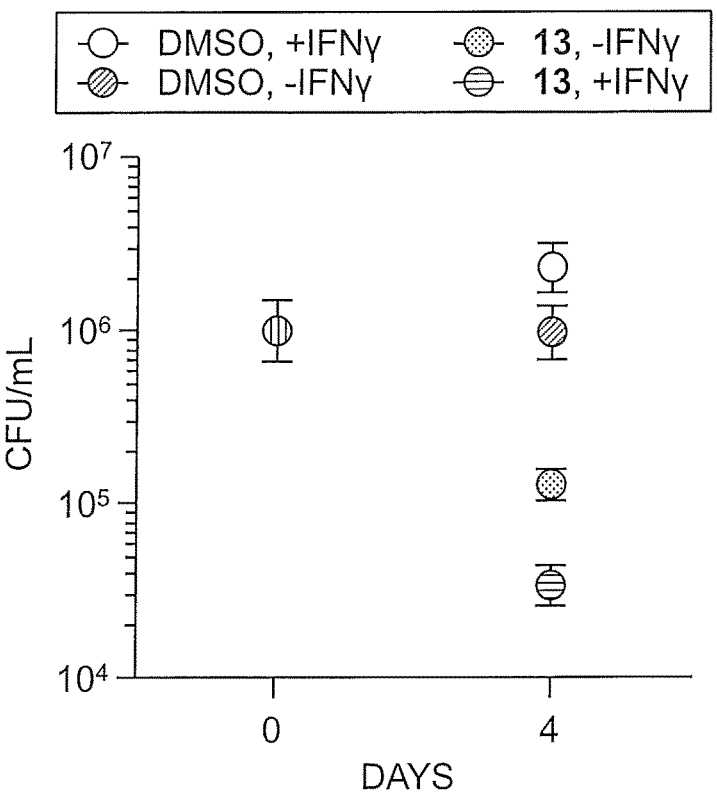
FIG. 2 shows that compound 13 (100 μg/mL) kills wild-type Mtb infecting murine bone marrow-derived macrophages. Activation of the macrophages with 50 ng/mL IFNγ leads to improved killing with compound 13 by day 4 of drug treatment, likely due to production of nitric oxide and phagosomal acidification.

The four-stress NR model of NaNO$_2$, mild acid, hypoxia, and a fatty acid carbon source was designed to replicate conditions encountered by Mtb in an activated macrophage phagosome. The combination of Mtb and interferon gamma (IFNγ) potently activates the inducible nitric oxide synthase (iNOS) and acidifies the phagosomal compartment to ~pH 4.5. Thus, it was expected that compounds of the invention with NR activity would also be active against Mtb infecting murine bone marrow-derived macrophages (BMDMs) activated with IFNγ. Accordingly, BMDMs were infected at a multiplicity of infection (MOI) of 5, and after 4-6 hours of Mtb uptake into the macrophages, were washed to remove away any remaining extracellular bacteria. Treatment with 100 μg/mL compound 13 subsequently commenced. After two days, the macrophage medium was partly exchanged for fresh medium (50%) and fresh compound 13. In two independent experiments, killing of intracellular Mtb (~1.5 log$_{10}$ reduction of CFU in activated macrophages) was observed. By visual inspection at 400× magnification, there was no toxicity of compound 13 to the macrophages. The killing potential of compound 13 was further tested against Mtb in both unactivated macrophages (−IFNγ) and activated macrophages (+50 ng/mL IFNγ) (FIG. 2). Increased killing by compound 13 in IFNγ-activated BMDMs (approximately 0.5 log$_{10}$) was observed, which is consistent with the preference of compound 13 for mild acid and nitric oxide to kill.

EXAMPLE 9

NR-Active Cephalosporins Lack Broad Spectrum Activity

Many β-lactams possess broad-spectrum activity against bacteria with a peptidoglycan cell wall. To explore this, compound 13 was tested for activity against a panel of Gram-negative (*Escherichia coli, Pseudomonas aeruginosa*) and Gram-positive (*Streptococcus, Staphylococcus aureus*) bacterial pathogens in replicating conditions (Table 4). In addition, activity was tested against the fungus *Candida albicans* at pH 5.0. Compound 13 had MIC's of >100 μg/mL against all five strains; compound 11c and compound 12b had MIC's of >100 μg/mL against the four bacteria and was not tested against *C. albicans*. These data are consistent with the NR-active cephalosporins having a narrow spectrum of activity against non-replicating *Mycobacterium tuberculosis*.

What is claimed is:

1. A compound having the structure of Formula I or V, or a pharmaceutically acceptable salt thereof:

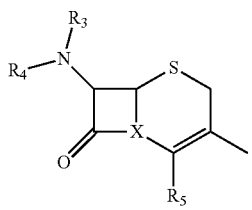

Formula I

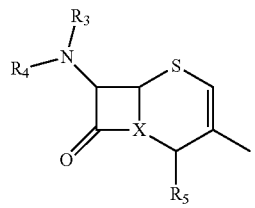

Formula V wherein
X is N;
R$_3$ is H, CH$_3$ or —CR$_7$;
R$_4$ is C$_1$-C$_{10}$ alkyl, —COO⁻, —COOH, —CR$_7$, —C(=O)OR$_7$, —C(=O)OCR$_7$, —C(=O)C(—CH$_3$)OR$_7$, —CH$_2$OR$_7$, —C(=O)CH$_2$CH$_2$R$_7$ or —NHR$_6$;
R$_5$ is C$_1$-C$_{10}$ alkyl, —CR$_7$, —C(=O)COR$_7$, —C(=O)C(—CH$_3$)OR$_7$, —CH$_2$OR$_7$, or —NHR$_6$;
R$_6$ is C$_1$-C$_{10}$ alkyl, C$_3$-C$_7$ cycloalkyl, aryl, heteroaryl, or —CR$_7$; and
R$_7$ is C$_2$-C$_{10}$ alkyl, C$_2$-C$_{10}$ alkenyl, C$_2$-C$_{10}$ alkynyl, C$_3$-C$_7$ cycloalkyl, unsubstituted aryl, heteroaryl or aryl substituted with an alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, alkoxyalkoxy, acyl, halo, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, or heterocyclyl group.

2. A pharmaceutical composition for killing or inhibiting the spread of a microorganism comprising one or more compounds having the structure of Formula I or V, or a pharmaceutically acceptable salt thereof, in admixture with a pharmaceutically acceptable carrier,

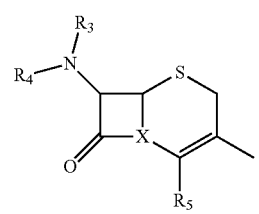

Formula I

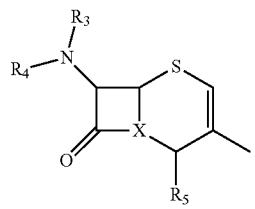

Formula V wherein
X is N;
R$_3$ is H, CH$_3$ or —CR$_7$;
R$_4$ is C$_1$-C$_{10}$ alkyl, —COO⁻, —COOH, —CR$_7$, —C(=O)OR$_7$, —C(=O)OCR$_7$, —C(=O)C(—CH$_3$)OR$_7$, —CH$_2$OR$_7$, —C(=O)CH$_2$CH$_2$R$_7$ or —NHR$_6$;
R$_5$ is C$_1$-C$_{10}$ alkyl, —CR$_7$, —C(=O)OR$_7$, —C(=O)COR$_7$, —C(=O)OCR$_7$, —C(=O)C(—CH$_3$)OR$_7$, —CH$_2$OR$_7$, —C(=O)CH$_2$CH$_2$R$_7$ or —NHR$_6$;

$R_6$ is $C_1$-$C_{10}$ alkyl, $C_3$-$C_7$ cycloalkyl, aryl, heteroaryl, or —$CR_7$; and $R_7$ is $C_2$-$C_{10}$ alkyl, $C_2$-$C_{10}$ alkenyl, $C_2$-$C_{10}$ alkynyl, $C_3$-$C_7$ cycloalkyl, aryl, or heteroaryl.

3. The pharmaceutical composition of claim 2, further comprising one or more antitubercular agents.

4. The compound of claim 1, wherein:
X is N;
$R_3$ is H, $CH_3$ or —$CR_7$;
$R_4$ is —COO$^-$, —COOH, —C(=O)O$R_7$, —C(=O)OC$R_7$, —C(=O)C(—$CH_3$)O$R_7$, or —C(=O)CH$_2$CH$_2$$R_7$;
$R_5$ is —C(=O)CO$R_7$, or —C(=O)C(—$CH_3$)O$R_7$; and
$R_7$ is $C_2$-$C_{10}$ alkyl, $C_2$-$C_{10}$ alkenyl, $C_2$-$C_{10}$ alkynyl, $C_3$-$C_7$ cycloalkyl, unsubstituted aryl, or heteroaryl or aryl substituted with an alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, alkoxyalkoxy, acyl, halo, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, or heterocyclyl group.

5. The pharmaceutical composition of claim 2, wherein:
X is N;
$R_3$ is H, $CH_3$ or —$CR_7$;
$R_4$ is —COO$^-$, —COOH, —C(=O)O$R_7$, —C(=O)OC$R_7$, —C(=O)C(—$CH_3$)O$R_7$, or —C(=O)CH$_2$CH$_2$$R_7$;
$R_5$ is —C(=O)O$R_7$, —C(=O)CO$R_7$, —C(=O)OC$R_7$, —C(=O)C(—$CH_3$)O$R_7$, or —C(=O)CH$_2$CH$_2$$R_7$; and
$R_7$ is $C_2$-$C_{10}$ alkyl, $C_2$-$C_{10}$ alkenyl, $C_2$-$C_{10}$ alkynyl, $C_3$-$C_7$ cycloalkyl, aryl, or heteroaryl.

6. A pharmaceutical composition for killing or inhibiting the spread of a microorganism comprising a compound having the structure:

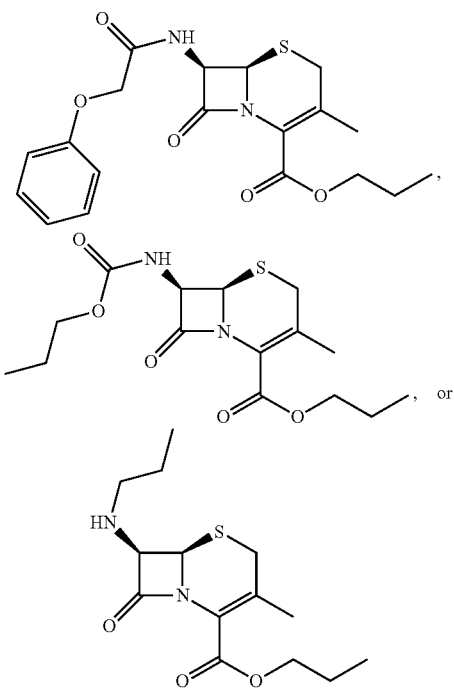

or a pharmaceutically acceptable salt thereof, in admixture with a pharmaceutically acceptable carrier.

* * * * *